US012575928B2

(12) United States Patent
Sands et al.

(10) Patent No.: US 12,575,928 B2
(45) Date of Patent: Mar. 17, 2026

(54) DEVICES, SYSTEMS, AND METHODS FOR AN IMPLANTABLE HEART-VALVE ADAPTER

(71) Applicant: ReValve Solutions Inc., Irvine, CA (US)

(72) Inventors: Julie Logan Sands, McLean, VA (US); Kenneth Eugene Perry, Irvine, CA (US); Anthony Zoltan Zador, Irvine, CA (US)

(73) Assignee: ReValve Solutions, Inc., Irvine, CA (US)

( * ) Notice: Subject to any disclaimer, the term of this patent is extended or adjusted under 35 U.S.C. 154(b) by 0 days.

(21) Appl. No.: 18/028,212

(22) PCT Filed: Sep. 23, 2021

(86) PCT No.: PCT/US2021/051828
§ 371 (c)(1),
(2) Date: Mar. 23, 2023

(87) PCT Pub. No.: WO2022/066961
PCT Pub. Date: Mar. 31, 2022

(65) Prior Publication Data
US 2023/0372085 A1     Nov. 23, 2023

Related U.S. Application Data

(60) Provisional application No. 63/082,035, filed on Sep. 23, 2020.

(51) Int. Cl.
*A61F 2/24*          (2006.01)

(52) U.S. Cl.
CPC .......... *A61F 2/2418* (2013.01); *A61F 2/2439* (2013.01); *A61F 2/2409* (2013.01); *A61F 2210/0014* (2013.01); *A61F 2220/0016* (2013.01); *A61F 2220/0075* (2013.01); *A61F 2230/0069* (2013.01); *A61F 2250/001* (2013.01); *A61F 2250/0039* (2013.01); *A61F 2250/006* (2013.01)

(58) Field of Classification Search
CPC ............................. A61F 2/2418; A61F 2/2439
See application file for complete search history.

(56)          References Cited

U.S. PATENT DOCUMENTS

| | | |
|---|---|---|
| 5,980,564 A | 11/1999 | Stinson |
| 6,290,674 B1 | 9/2001 | Roue et al. |
| 6,306,133 B1 | 10/2001 | Tu et al. |
| 6,632,241 B1 | 10/2003 | Hancock et al. |
| 7,018,401 B1 | 3/2006 | Hyodoh et al. |
| 7,329,279 B2 | 2/2008 | Haug et al. |

(Continued)

FOREIGN PATENT DOCUMENTS

| | | |
|---|---|---|
| CA | 2623814 C | 4/2014 |
| CN | 106943207 A | 11/2018 |

(Continued)

*Primary Examiner* — Suba Ganesan
(74) *Attorney, Agent, or Firm* — Perkins Coie LLP

(57)          ABSTRACT

Devices, systems, and methods for an implantable heart-valve adapter that enables compact and secure delivery into the heart and allows for convenient control of both the adapter during implantation as well as the expansion and retraction of the valve when implanted, removed, or replaced.

18 Claims, 29 Drawing Sheets

(56) References Cited

U.S. PATENT DOCUMENTS

| | | | |
|---|---|---|---|
| 7,338,466 B2 | 3/2008 | Hart et al. |
| 7,556,646 B2 | 7/2009 | Yang et al. |
| 7,947,075 B2 | 5/2011 | Goetz et al. |
| 8,167,932 B2 | 5/2012 | Bourang et al. |
| 8,403,983 B2 | 3/2013 | Quadri et al. |
| 8,449,599 B2 | 5/2013 | Chau et al. |
| 8,500,798 B2 | 8/2013 | Rowe et al. |
| 8,568,472 B2 | 10/2013 | Marchand et al. |
| 8,568,475 B2 | 10/2013 | Nguyen et al. |
| 8,585,755 B2 | 11/2013 | Chau et al. |
| 8,628,571 B1 | 1/2014 | Hacohen et al. |
| 8,673,000 B2 | 3/2014 | Tabor et al. |
| 8,840,663 B2 | 9/2014 | Salahieh et al. |
| 8,858,621 B2 | 10/2014 | Oba et al. |
| 8,926,691 B2 | 1/2015 | Chau et al. |
| 8,992,604 B2 | 3/2015 | Gross et al. |
| 9,084,676 B2 | 7/2015 | Chau et al. |
| 9,168,131 B2 | 10/2015 | Yohanan et al. |
| 9,532,870 B2 | 1/2017 | Cooper et al. |
| 9,717,591 B2 | 8/2017 | Chau et al. |
| 9,744,031 B2 | 8/2017 | Girard et al. |
| 9,763,657 B2 | 9/2017 | Hacohen et al. |
| 9,763,778 B2 | 9/2017 | Eidenschink et al. |
| 9,763,780 B2 | 9/2017 | Morriss et al. |
| 9,867,700 B2 | 1/2018 | Bakis et al. |
| 9,867,704 B2 | 1/2018 | Lee et al. |
| 9,907,652 B2 | 3/2018 | Chau et al. |
| 9,962,260 B2 | 5/2018 | Krans et al. |
| 10,034,746 B2 | 7/2018 | Figulla et al. |
| 10,092,400 B2 | 10/2018 | Jimenez et al. |
| 10,111,748 B2 | 10/2018 | Chau et al. |
| 10,376,363 B2 | 8/2019 | Quadri et al. |
| 10,463,489 B2 | 11/2019 | Christianson et al. |
| 10,470,876 B2 | 11/2019 | Gurovich et al. |
| 10,531,951 B2 | 1/2020 | Spargias |
| 10,583,001 B2 | 3/2020 | Navia et al. |
| 10,743,992 B2 | 8/2020 | Krans et al. |
| 10,813,757 B2 | 10/2020 | Cooper et al. |
| 11,039,917 B2 | 6/2021 | Bruchman et al. |
| 11,123,186 B2 | 9/2021 | Landon et al. |
| 11,202,704 B2 | 12/2021 | Morriss et al. |
| 11,253,364 B2 | 2/2022 | Cooper et al. |
| 11,278,398 B2 | 3/2022 | Salahieh et al. |
| 11,872,123 B2 | 1/2024 | Schmitt |
| 2002/0099432 A1 | 7/2002 | Yee |
| 2004/0186549 A1 | 9/2004 | Jayaraman |
| 2004/0243230 A1 | 12/2004 | Navia et al. |
| 2005/0137688 A1 | 6/2005 | Salahieh et al. |
| 2005/0137689 A1 | 6/2005 | Salahieh et al. |
| 2005/0137691 A1 | 6/2005 | Salahieh et al. |
| 2005/0137693 A1 | 6/2005 | Haug et al. |
| 2005/0283231 A1 | 12/2005 | Haug et al. |
| 2006/0058872 A1 | 3/2006 | Salahieh et al. |
| 2006/0135968 A1 | 6/2006 | Schaller |
| 2007/0093869 A1 | 4/2007 | Bloom et al. |
| 2007/0244552 A1 | 10/2007 | Salahieh et al. |
| 2008/0221670 A1 | 9/2008 | Clerc et al. |
| 2008/0275540 A1 | 11/2008 | Wen |
| 2008/0300673 A1 | 12/2008 | Clerc et al. |
| 2009/0093826 A1 | 4/2009 | Warder-Gabaldon |
| 2009/0149872 A1 | 6/2009 | Gross et al. |
| 2009/0182404 A1 | 7/2009 | Shokoohi |
| 2009/0198315 A1 | 8/2009 | Boudjemline |
| 2010/0049313 A1 | 2/2010 | Alon et al. |
| 2011/0004299 A1 | 1/2011 | Navia et al. |
| 2011/0166636 A1 | 7/2011 | Rowe |
| 2011/0319988 A1 | 12/2011 | Schankereli et al. |
| 2012/0101571 A1 | 4/2012 | Thambar et al. |
| 2013/0018457 A1 | 1/2013 | Gregg et al. |
| 2013/0123912 A1 | 5/2013 | Tung et al. |
| 2013/0172992 A1 | 7/2013 | Gross et al. |
| 2013/0197629 A1 | 8/2013 | Gainor et al. |
| 2013/0304200 A1 | 11/2013 | McLean et al. |
| 2013/0338684 A1 | 12/2013 | Hausen |
| 2014/0005777 A1 | 1/2014 | Anderl et al. |

| | | | |
|---|---|---|---|
| 2014/0088696 A1* | 3/2014 | Figulla ................ A61F 2/2418 |
| | | | 623/2.17 |
| 2014/0172083 A1 | 6/2014 | Bruchman et al. |
| 2014/0180014 A1 | 6/2014 | Ransden et al. |
| 2014/0296969 A1 | 10/2014 | Tegels et al. |
| 2014/0316516 A1 | 10/2014 | Vidlund et al. |
| 2014/0324164 A1* | 10/2014 | Gross ................... A61F 2/2418 |
| | | | 623/2.37 |
| 2014/0371844 A1 | 12/2014 | Dale et al. |
| 2015/0142103 A1 | 5/2015 | Vidlund |
| 2015/0223934 A1 | 8/2015 | Vidlund et al. |
| 2015/0272731 A1 | 10/2015 | Racchini et al. |
| 2015/0327994 A1 | 11/2015 | Morriss et al. |
| 2015/0359629 A1 | 12/2015 | Ganesan et al. |
| 2016/0089233 A1 | 3/2016 | Lee et al. |
| 2016/0256270 A1 | 9/2016 | Folan et al. |
| 2016/0310268 A1 | 10/2016 | Oba et al. |
| 2016/0331529 A1* | 11/2016 | Marchand ............ A61F 2/2436 |
| 2017/0056175 A1 | 3/2017 | Chin et al. |
| 2017/0071766 A1 | 3/2017 | Düring et al. |
| 2017/0165066 A1 | 6/2017 | Rothstein |
| 2017/0172737 A1 | 6/2017 | Kuetting et al. |
| 2017/0189175 A1 | 7/2017 | Justino et al. |
| 2017/0266003 A1 | 9/2017 | Hammer et al. |
| 2017/0296332 A1 | 10/2017 | Harder |
| 2017/0367822 A1 | 12/2017 | Naor et al. |
| 2018/0049868 A1 | 2/2018 | Board et al. |
| 2018/0049873 A1 | 2/2018 | Manash et al. |
| 2018/0055629 A1 | 3/2018 | Oba et al. |
| 2018/0125647 A1 | 5/2018 | Nasr |
| 2018/0125648 A1 | 5/2018 | Nasr |
| 2018/0125649 A1 | 5/2018 | Nasr |
| 2018/0125650 A1 | 5/2018 | Nasr |
| 2018/0125651 A1 | 5/2018 | Nasr |
| 2018/0193138 A1 | 7/2018 | Vidlund |
| 2018/0250126 A1 | 9/2018 | Tim |
| 2018/0256321 A1 | 9/2018 | Zhang et al. |
| 2018/0256327 A1 | 9/2018 | Perszyk et al. |
| 2018/0325660 A1 | 11/2018 | Mauch et al. |
| 2018/0325664 A1 | 11/2018 | Gonda et al. |
| 2019/0053897 A1 | 2/2019 | Levi et al. |
| 2019/0060060 A1 | 2/2019 | Chau et al. |
| 2019/0209311 A1 | 7/2019 | Zhang et al. |
| 2019/0240006 A1 | 8/2019 | Chodór |
| 2019/0240008 A1 | 8/2019 | Salahieh et al. |
| 2019/0254816 A1 | 8/2019 | Anderson et al. |
| 2019/0269839 A1 | 9/2019 | Wilson et al. |
| 2020/0030092 A1* | 1/2020 | Tuval ................... A61F 2/2418 |
| 2020/0163761 A1 | 5/2020 | Hariton et al. |
| 2020/0253728 A1 | 8/2020 | Tayeb et al. |
| 2020/0276014 A1 | 9/2020 | Burkart et al. |
| 2020/0306037 A1 | 10/2020 | Siegel et al. |
| 2020/0375731 A1 | 12/2020 | Ratz et al. |
| 2021/0000593 A1 | 1/2021 | Rahmig et al. |
| 2021/0030536 A1 | 2/2021 | Kaleta |
| 2021/0068948 A1 | 3/2021 | Jimenez et al. |
| 2021/0068950 A1 | 3/2021 | Quill et al. |
| 2021/0077256 A1 | 3/2021 | Pellegrini et al. |
| 2021/0330455 A1 | 10/2021 | Sands et al. |
| 2022/0031452 A1 | 2/2022 | Alleleyn et al. |
| 2022/0117732 A1 | 4/2022 | Tuval et al. |
| 2022/0296367 A1 | 9/2022 | Hoang et al. |

FOREIGN PATENT DOCUMENTS

| | | | |
|---|---|---|---|
| DE | 102015209537 A1 | 11/2016 |
| EP | 2537487 B1 | 4/2013 |
| EP | 2921139 B1 | 11/2018 |
| EP | 4138735 A2 | 3/2023 |
| JP | 2007526011 A | 9/2007 |
| JP | 2008541865 A | 11/2008 |
| JP | 2011509806 A | 3/2011 |
| JP | 2012500665 A | 1/2012 |
| JP | 2013512765 A | 4/2013 |
| JP | 2018523553 A | 8/2018 |
| WO | 2014153267 A2 | 9/2014 |
| WO | 2016110613 A1 | 7/2016 |
| WO | 2020058534 A1 | 3/2020 |
| WO | 2020073981 A1 | 4/2020 |

(56)                    References Cited

FOREIGN PATENT DOCUMENTS

| WO | 2020109576 | A1 | 6/2020 |
| WO | 2020109596 | A1 | 6/2020 |
| WO | 2020157018 | A1 | 8/2020 |
| WO | 2021185528 | A1 | 9/2021 |

* cited by examiner

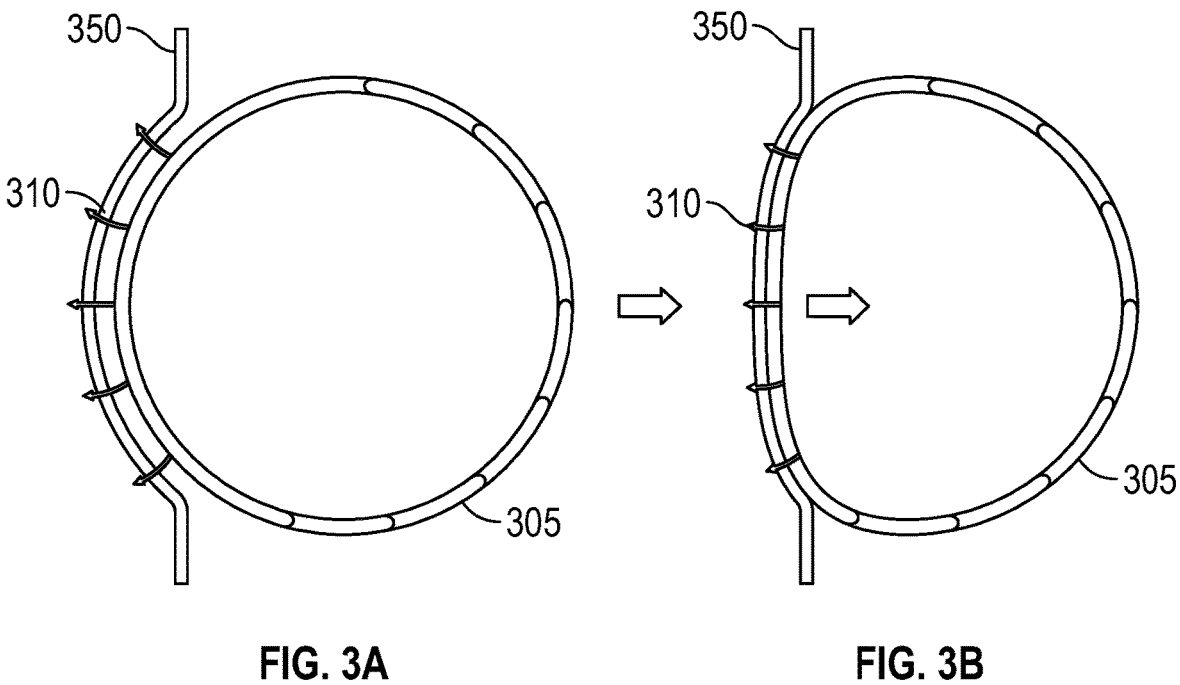
FIG. 3A                    FIG. 3B
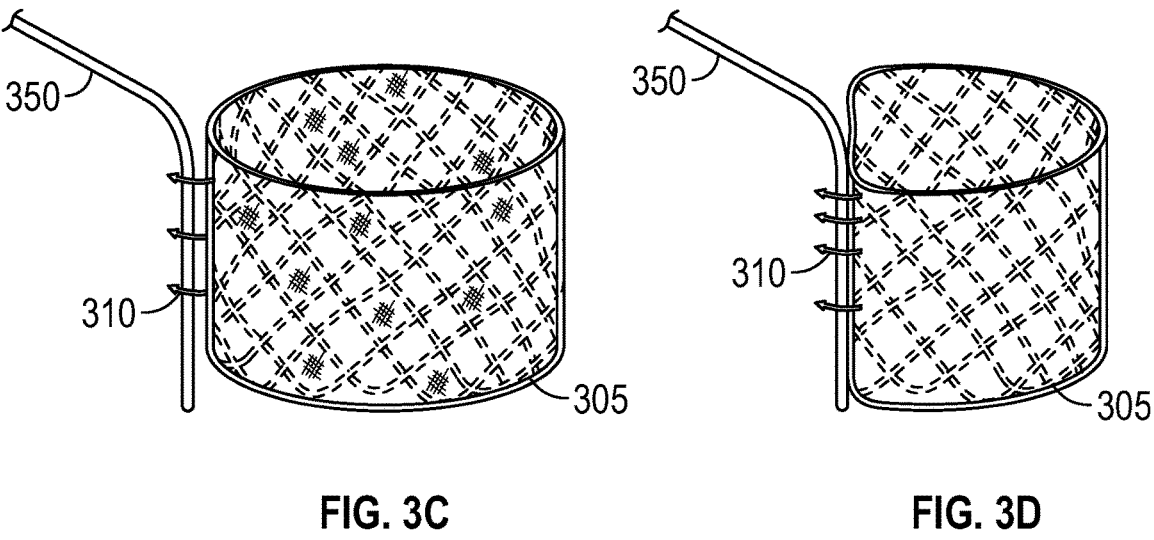
FIG. 3C                    FIG. 3D

910

910

1005

1010

1020

1015

1025

1030

1035

1040

1035

1105

1105

1105

1105

1905

DEVICES, SYSTEMS, AND METHODS FOR AN IMPLANTABLE HEART-VALVE ADAPTER

CROSS-REFERENCE TO RELATED APPLICATIONS

This application is a U.S. National Stage Application of International Patent Application No. PCT/US2021/051828, filed on Sep. 23, 2021, entitled "Devices, Systems, and Methods for an Implantable Heart-Valve Adapter", which claims priority and benefit to U.S. Provisional Application No. 63/082,035, filed on Sep. 23, 2020, entitled "Devices, Systems, and Methods for a Mitral-Valve Adapter Attachment", the contents of which are incorporated herein by this reference as though set forth in their entirety.

FIELD OF USE

The present disclosure relates generally to replacement heart-valve technology and to devices, systems, and methods for an implantable heart-valve adapter, such as for a mitral valve; and more specifically to the implantation thereof to the intended therapeutic location. Characteristics of the disclosed heart-valve adapter include high flexibility, resiliency, conformality, and serving as a receiver for a replaceable heart valve.

BACKGROUND

Heart-valve intervention, such as full open-heart surgery, is often required to treat diseases of one or more of the four heart valves which work together to keep blood properly flowing through the heart. Replacement and/or repair of a heart valve is often required when a valve is "leaky" (e.g., there is valve regurgitation) or when a valve is narrowed and does not open properly (e.g., valve stenosis). Typically, heart-valve replacement, such as mitral-valve replacement, involves replacement of the heart's original (native) valve with a replacement mechanical and/or tissue (bioprosthetic) valve. Common problems with the replacement of valves and/or the frames carrying them include a) degradation of the leaflets (valve-like structure); b) breaking or failing frames, particularly with laser-cut nitinol frames; and c) undesirable changing in size of the native valve annulus. Replacement heart valves pose additional problems after they are implanted. For example, the replacement valve may move or migrate after it is placed in a desired location in the heart, or its location may not permit proper directional flow of blood through other parts of the organ such as the outflow tract of the left ventricle. Replacement valves are also not readily retrievable, most often because such removal can damage the surrounding heart tissue. This can be particularly problematic, for example, if the replacement valve is not properly and accurately placed into position when it is implanted in the native heart, as well as when the replacement valve starts failing, which may occur years after initial implantation. An additional problem is that typical replacement valves, especially laser-cut valve frames, are relatively stiff and inflexible, resulting in a valve that does not flex with the dynamic movements of the pumping heart. Such inflexible valves do not conform to such dynamic movements, which can cause trauma to the heart surfaces, cause breaks in the frame itself, otherwise cause or exacerbate problems during or after implantation.

Thus, what is needed are devices, systems, and methods for improving and facilitating valve implantation through a heart-valve adapter that enables compact and secure delivery into the heart and convenient control of both the adapter during implantation as well as the expansion and retraction of a valve when being implanted or removed/replaced, preferably entirely via a catheter. Also needed are devices, systems, and methods for ensuring proper directional flow of blood through the heart during and after a valve replacement procedure.

SUMMARY OF THE DISCLOSURE

The following presents a simplified overview of the example embodiments in order to provide a basic understanding of some embodiments of the present disclosure. This overview is not an extensive overview of the example embodiments. It is intended to neither identify key or critical elements of the example embodiments nor delineate the scope of the appended claims. Its sole purpose is to present some concepts of the example embodiments in a simplified form as a prelude to the more detailed description that is presented herein below. It is to be understood that both the following general description and the following detailed description are exemplary and explanatory only and are not restrictive.

The present disclosure is directed to devices, systems, and method for a heart-valve adapter ("Adapter") that serves the purpose of anchoring, sealing, and managing/controlling the position of the leaflets and sub-valvular structure. The Adapter is highly flexible, resilient, fatigue-resistant, and secures the receiver for the valve to the native valve tissue. As disclosed herein, the receiver portion of the Adapter receives a replacement heart valve that can be replaced years after implantation if problems, such as recurrent mitral valve regurgitation, arise.

Still other advantages, embodiments, and features of the subject disclosure will become readily apparent to those of ordinary skill in the art from the following description wherein there is shown and described a preferred embodiment of the present disclosure, simply by way of illustration of one of the best modes best suited to carry out the subject disclosure. As will be realized, the present disclosure is capable of other different embodiments and its several details are capable of modifications in various obvious embodiments all without departing from, or limiting, the scope herein. Accordingly, the drawings and descriptions will be regarded as illustrative in nature and not as restrictive.

BRIEF DESCRIPTION OF THE DRAWINGS

The accompanying drawings, which are incorporated in and constitute a part of this specification, illustrate embodiments of the disclosure and together with the general description of the disclosure given above and the detailed description of the drawings given below, serve to explain the principles of the disclosure. In certain instances, details that are not necessary for an understanding of the disclosure or that render other details difficult to perceive may have been omitted.

FIGS. 3A-3D generally illustrates an embodiment of a heart-valve adapter as disclosed herein.

3

Figure 5:
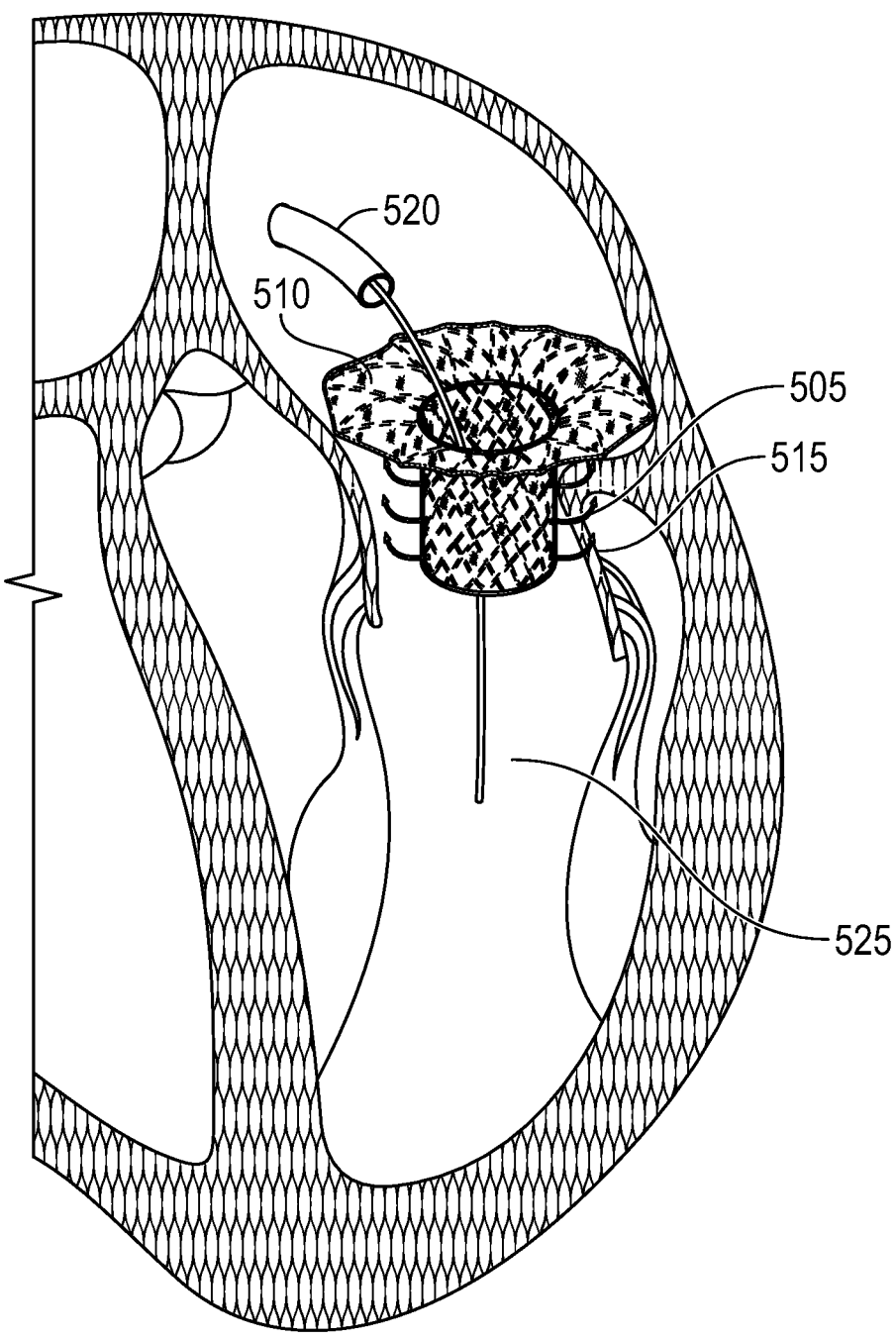

FIG. 5 generally illustrates an embodiment of a heart-valve adapter as disclosed herein.

Figure 6:
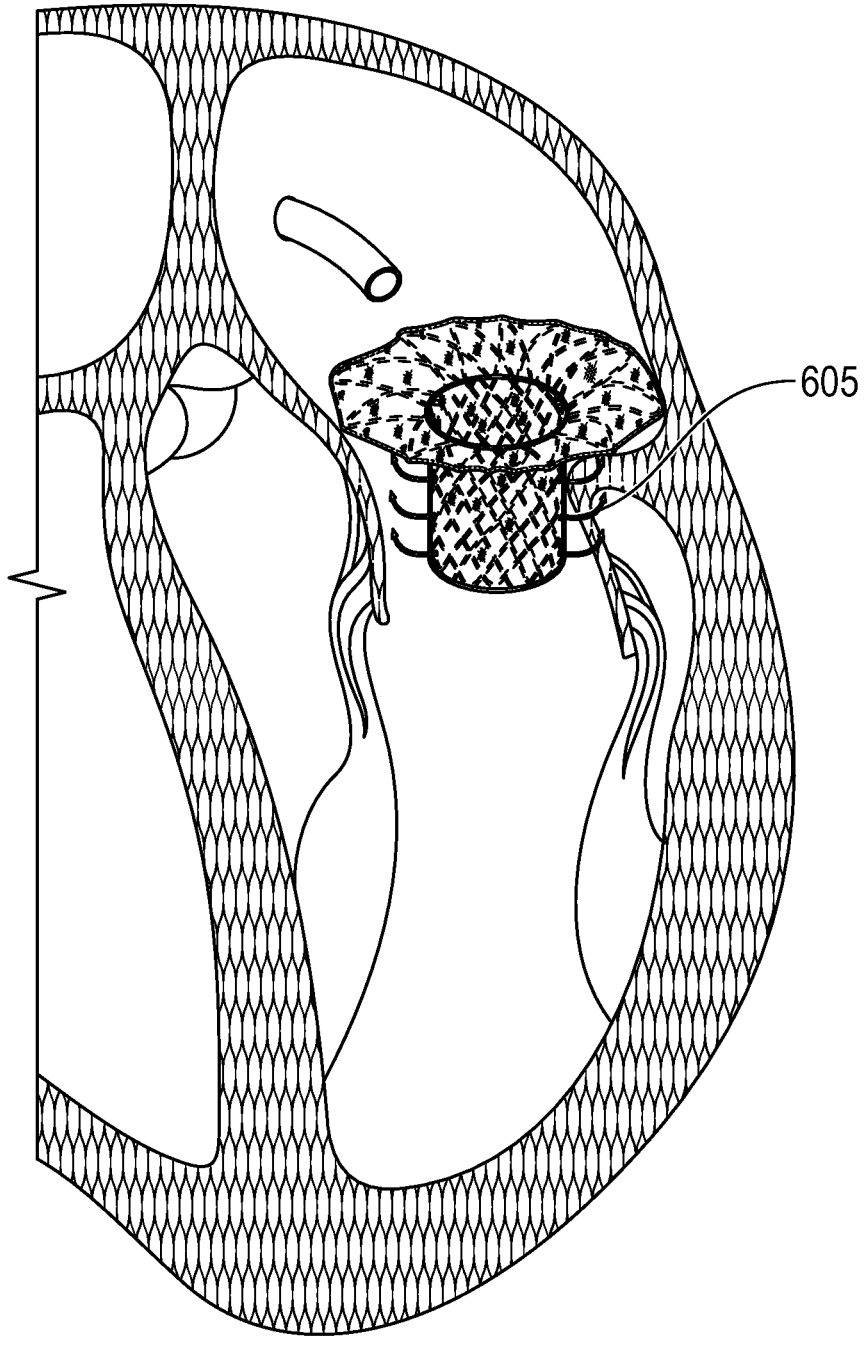

FIG. 6 generally illustrates an embodiment of a heart-valve adapter as disclosed herein.

Figure 7:
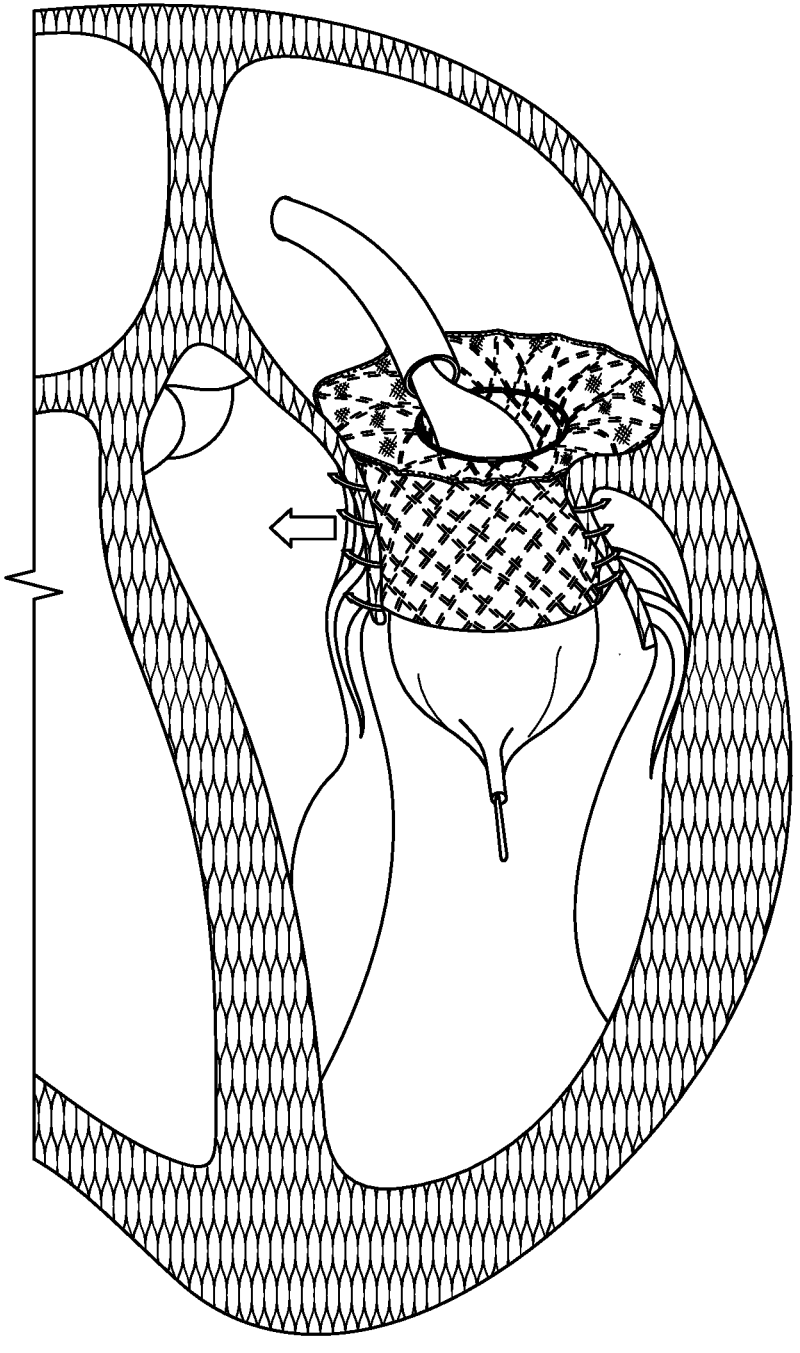

FIG. 7 generally illustrates an embodiment of a heart-valve adapter as disclosed herein.

Figure 8:
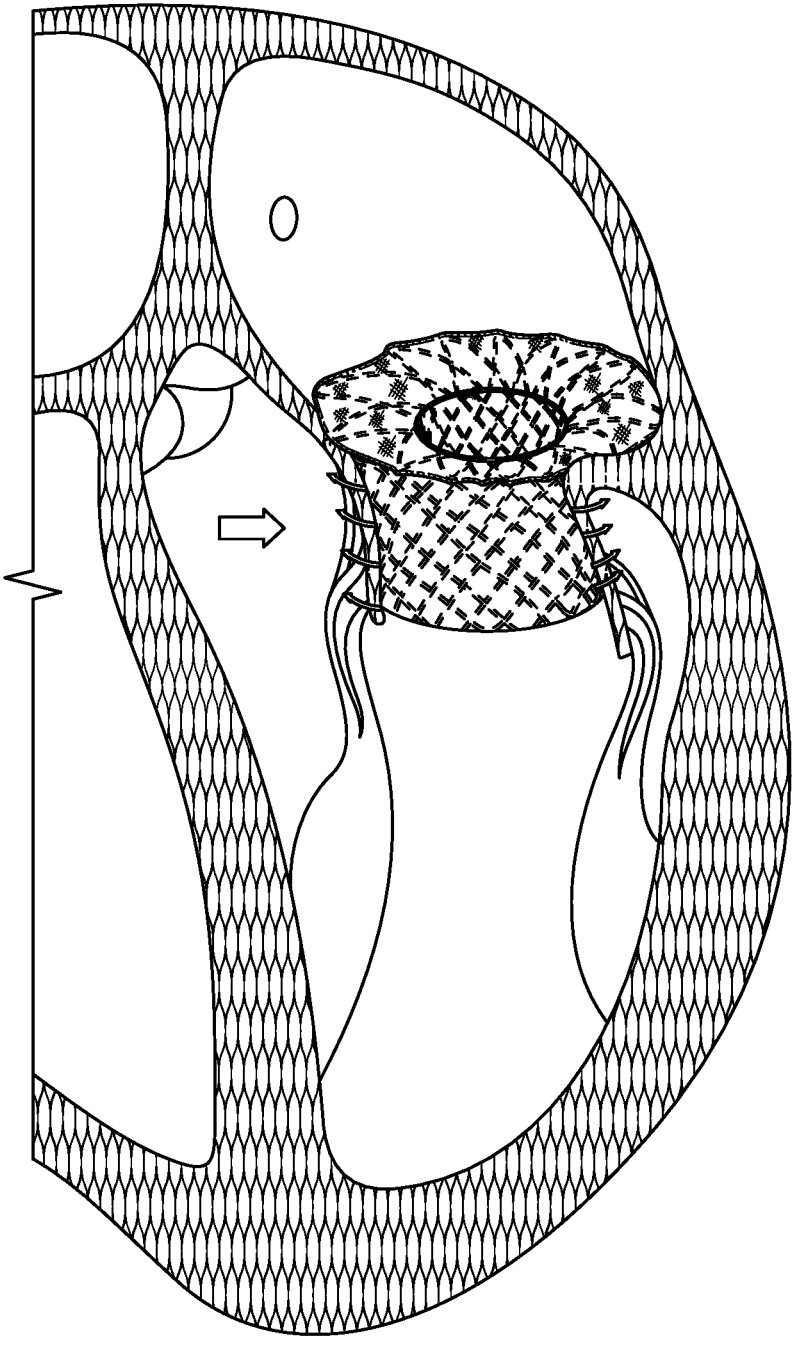

FIG. 8 generally illustrates an embodiment of a heart-valve adapter as disclosed herein.

Figure 9A:
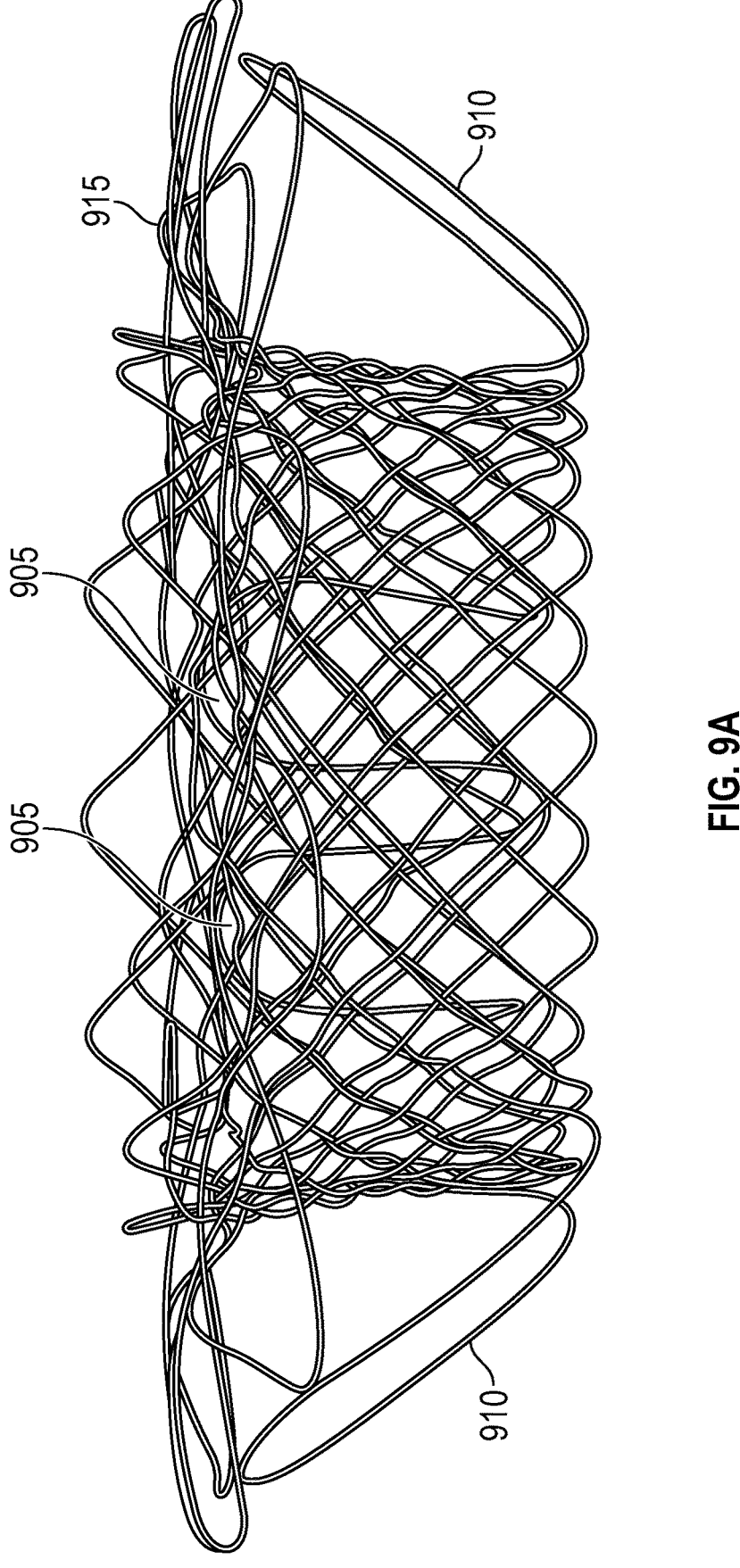
Figure 9B:
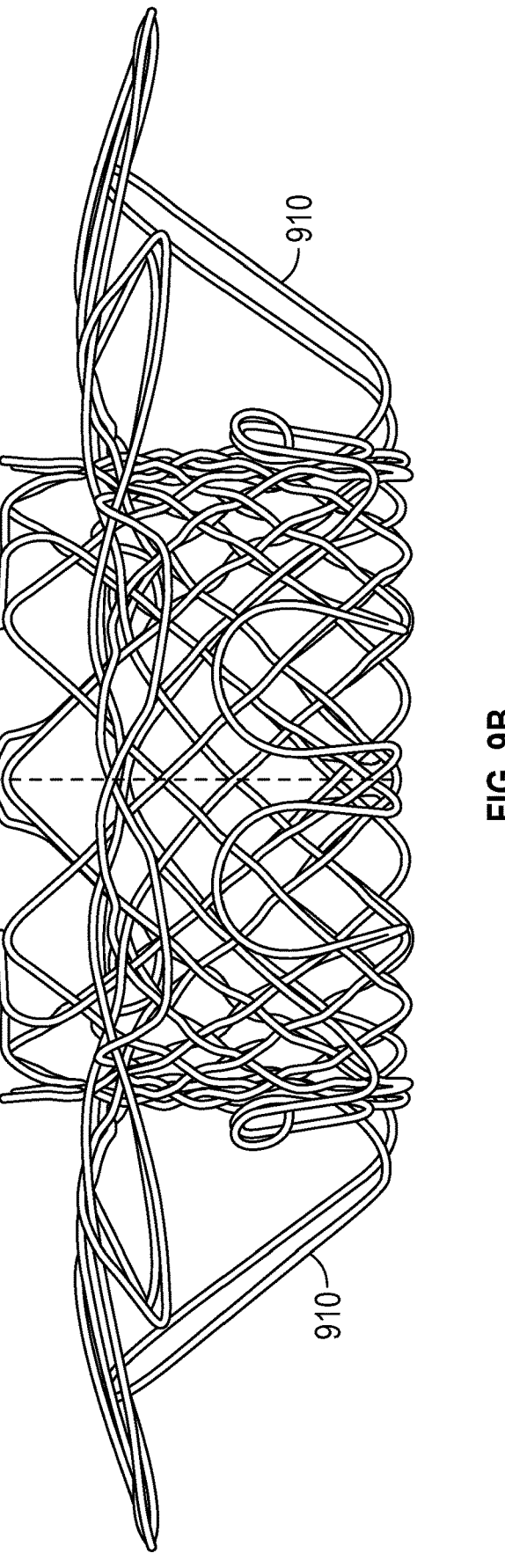
Figure 9C:
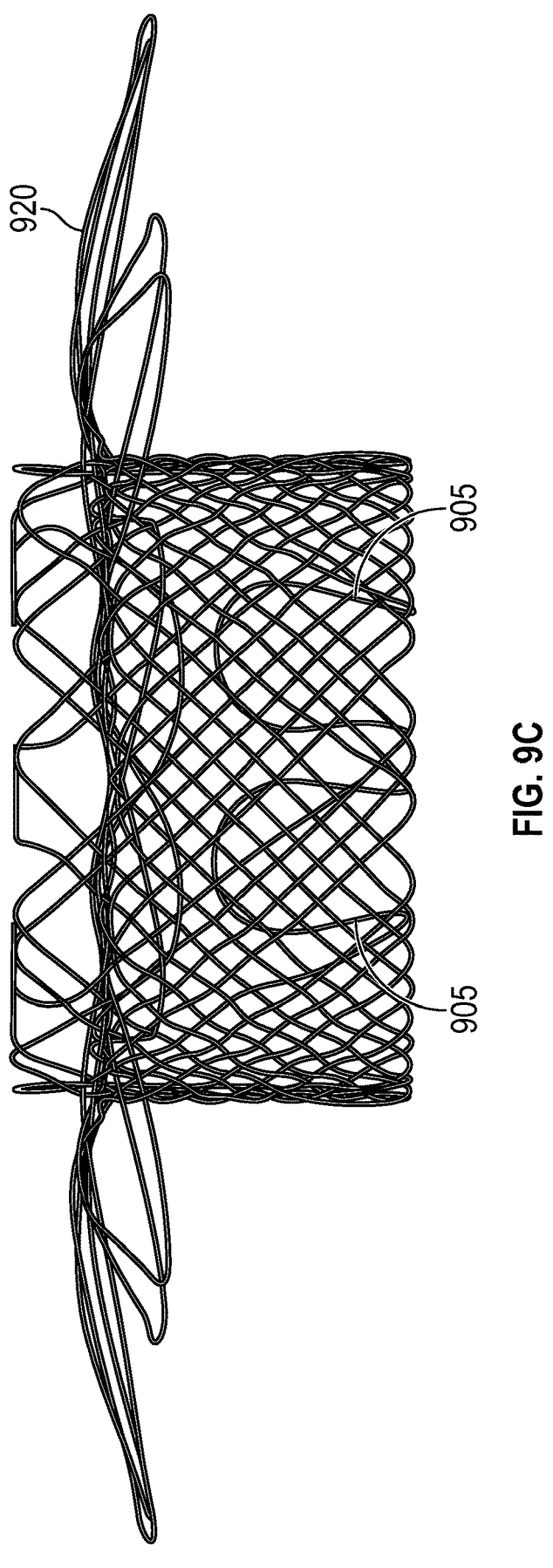

FIGS. 9A-9C generally illustrate an embodiment of a heart-valve adapter as disclosed herein.

FIGS. 10A-10E generally illustrate an embodiment of a heart-valve adapter as disclosed herein.

Figure 11A:
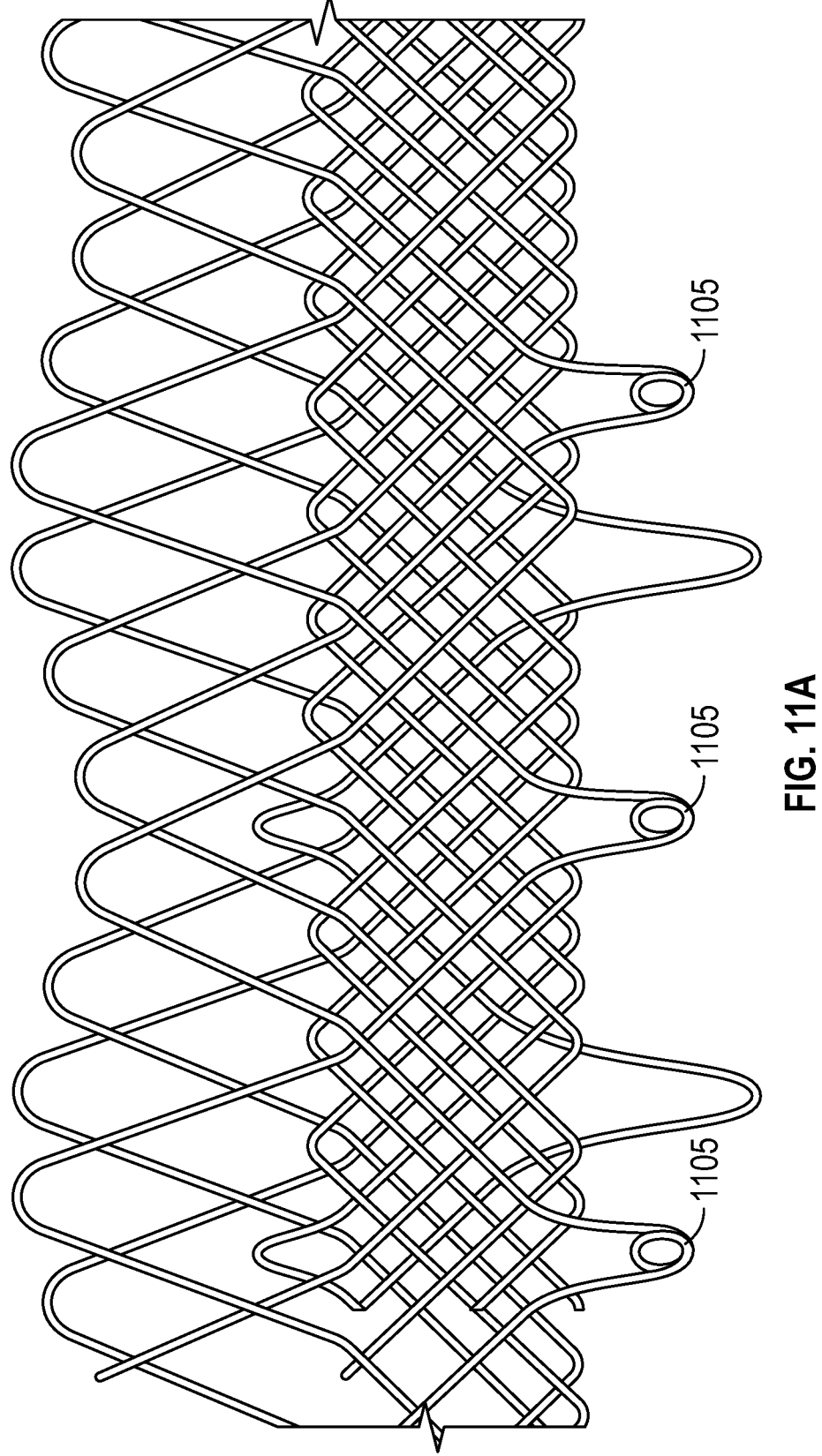
Figure 11B:
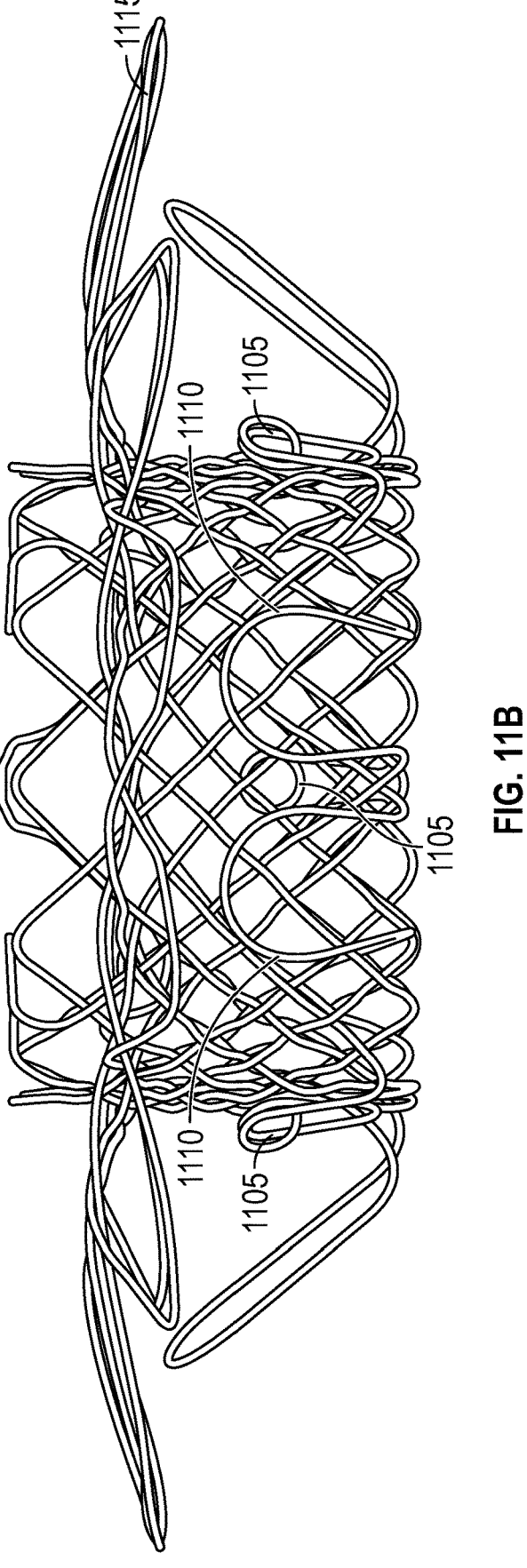
Figure 11C:
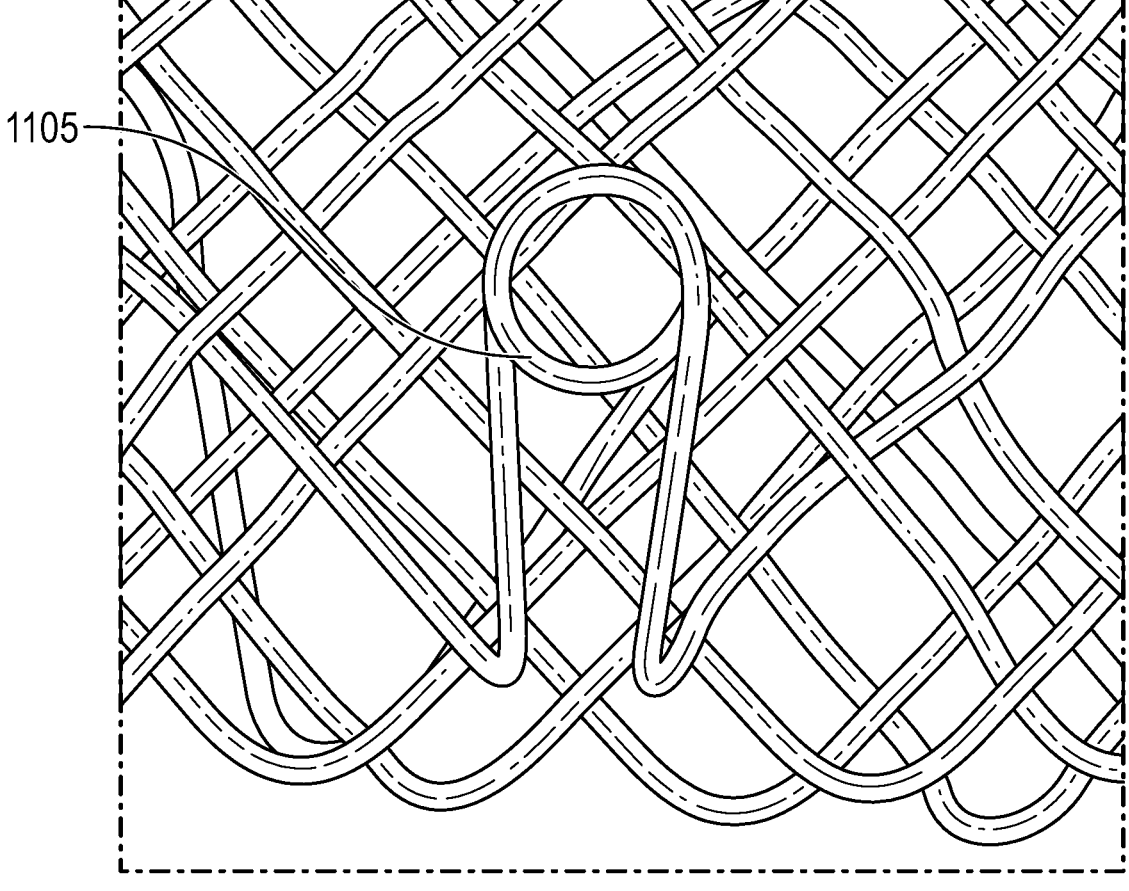

FIGS. 11A-11C generally illustrate an embodiment of a heart-valve adapter as disclosed herein.

Figure 12A:
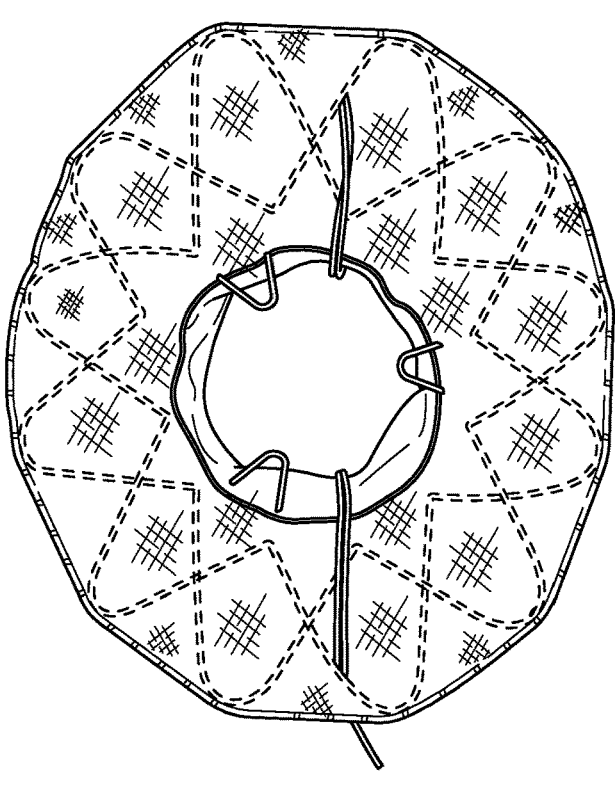
Figure 12B:
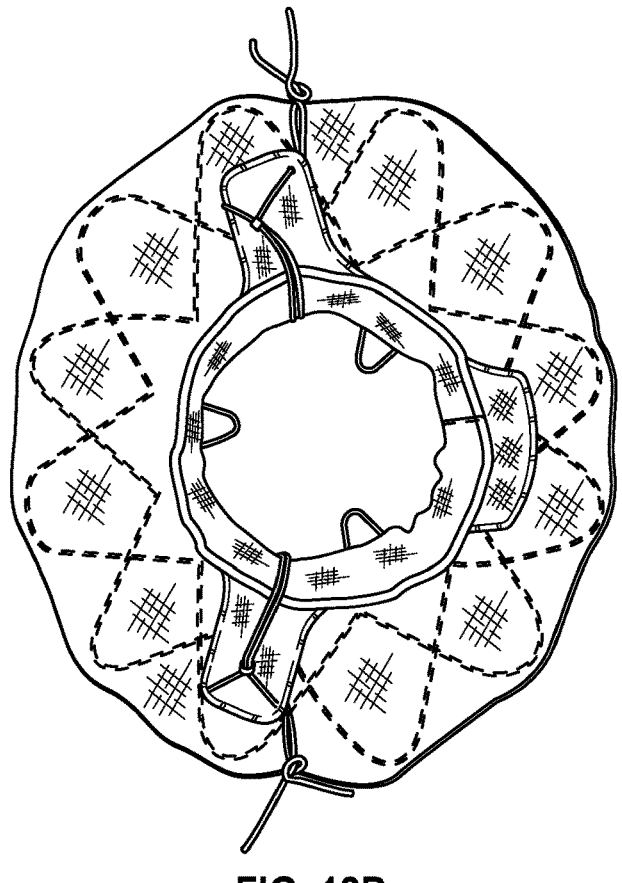

FIGS. 12A and 12B generally illustrate an embodiment of a heart-valve adapter as disclosed herein.

Figure 13A:
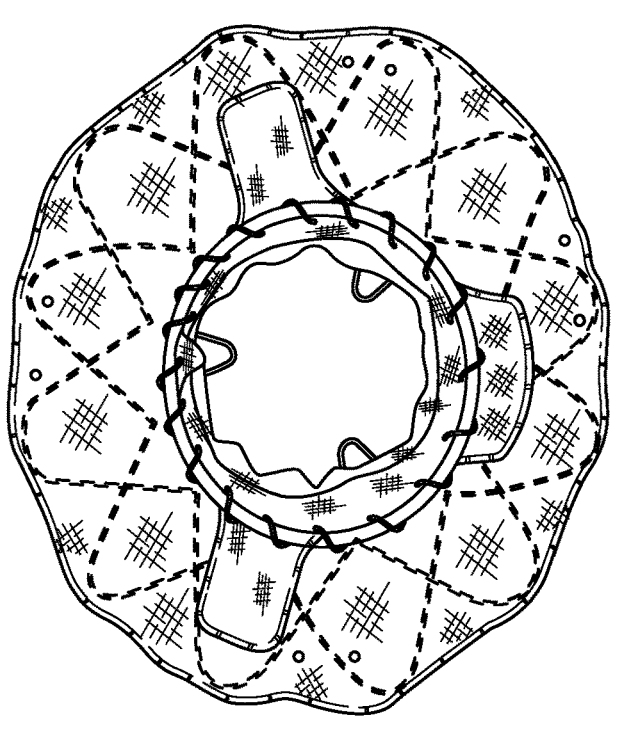
Figure 13B:
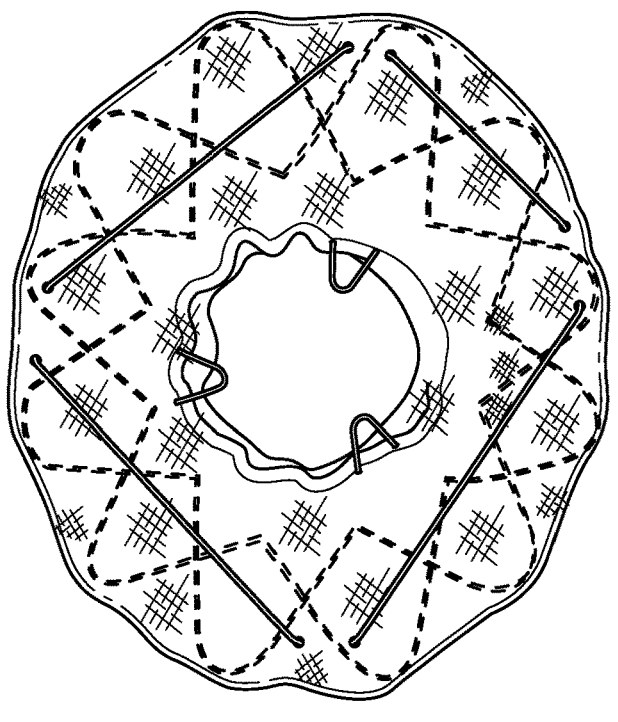
Figure 13C:
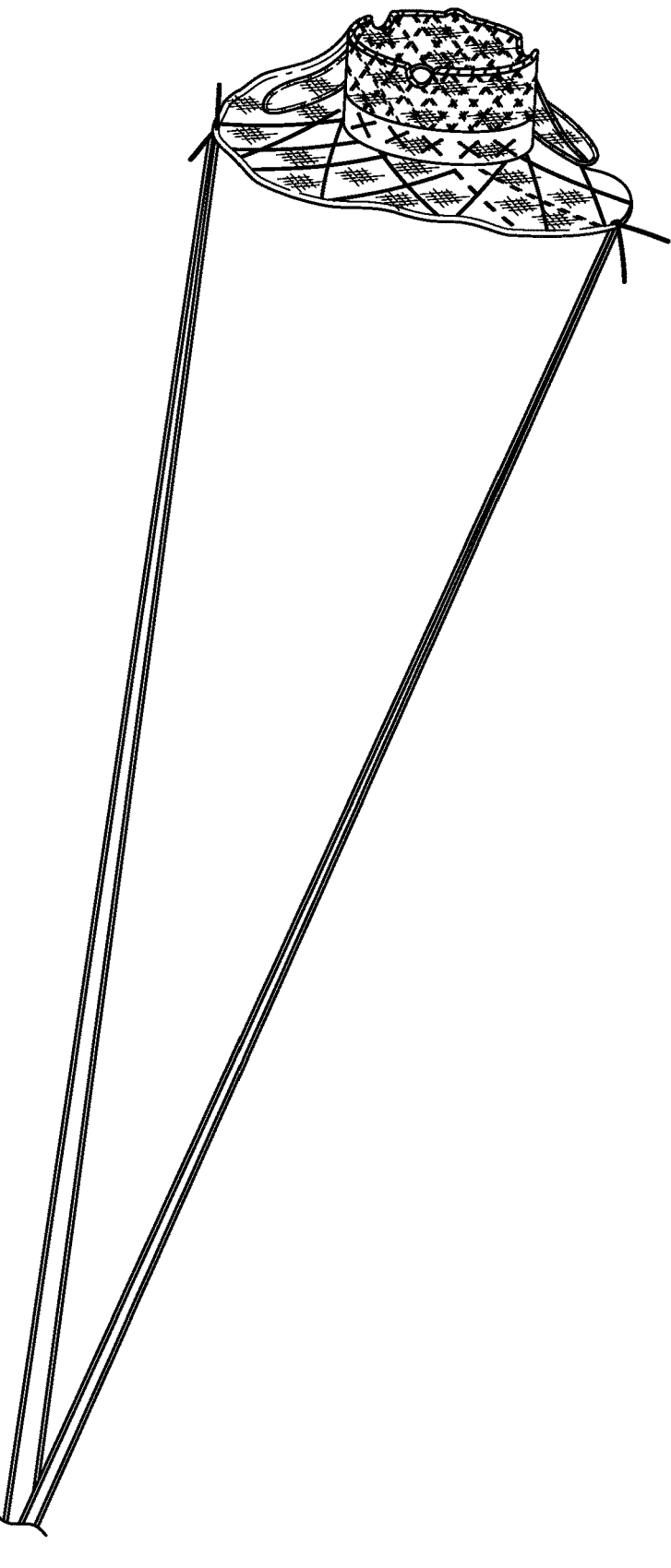
Figure 14A:
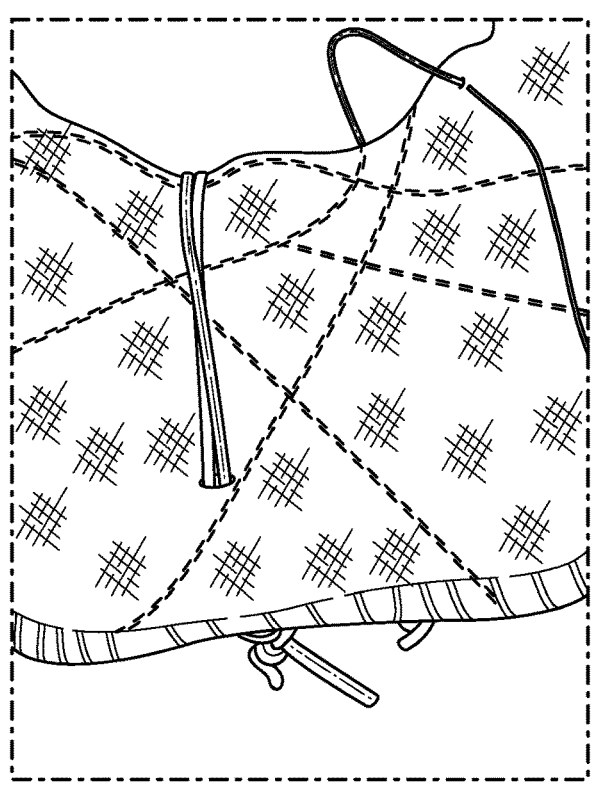
Figure 14B:
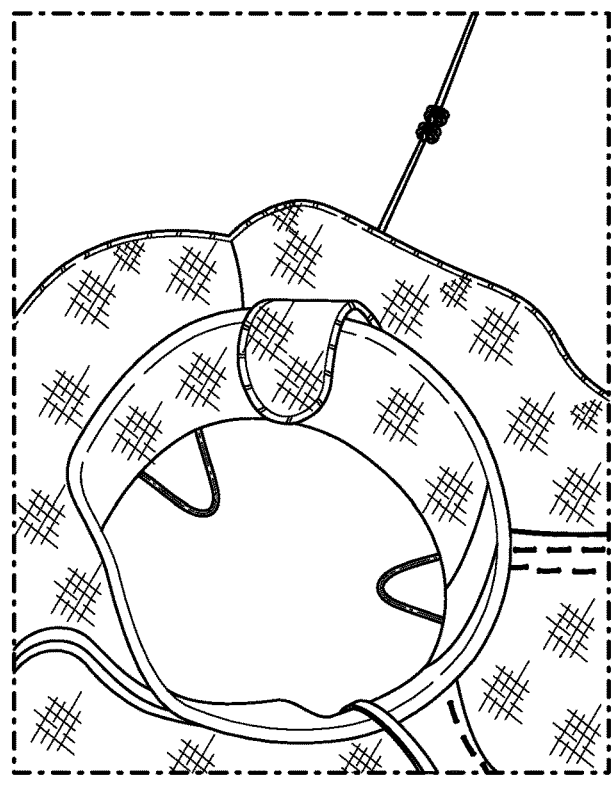
Figure 14C:
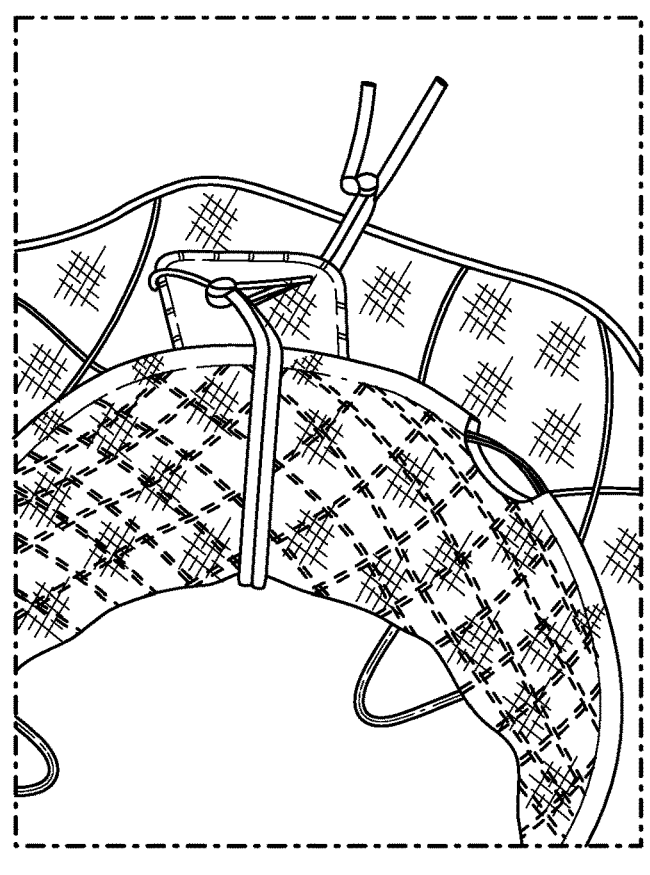
Figure 14D:
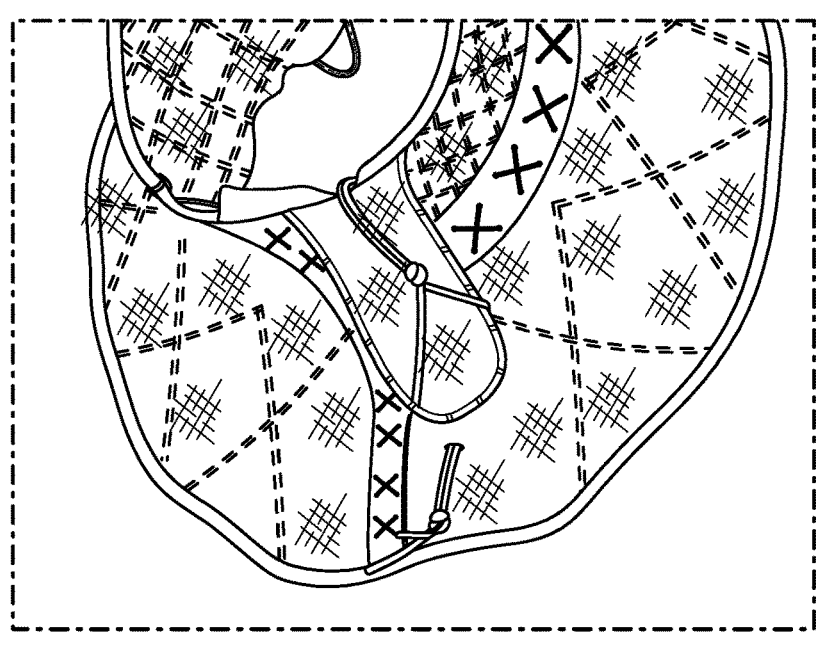

FIGS. 13A-13C generally illustrate an embodiment of a heart-valve adapter as disclosed herein.

FIGS. 14A-14D generally illustrate an embodiment of a heart-valve adapter as disclosed herein.

Figure 15:
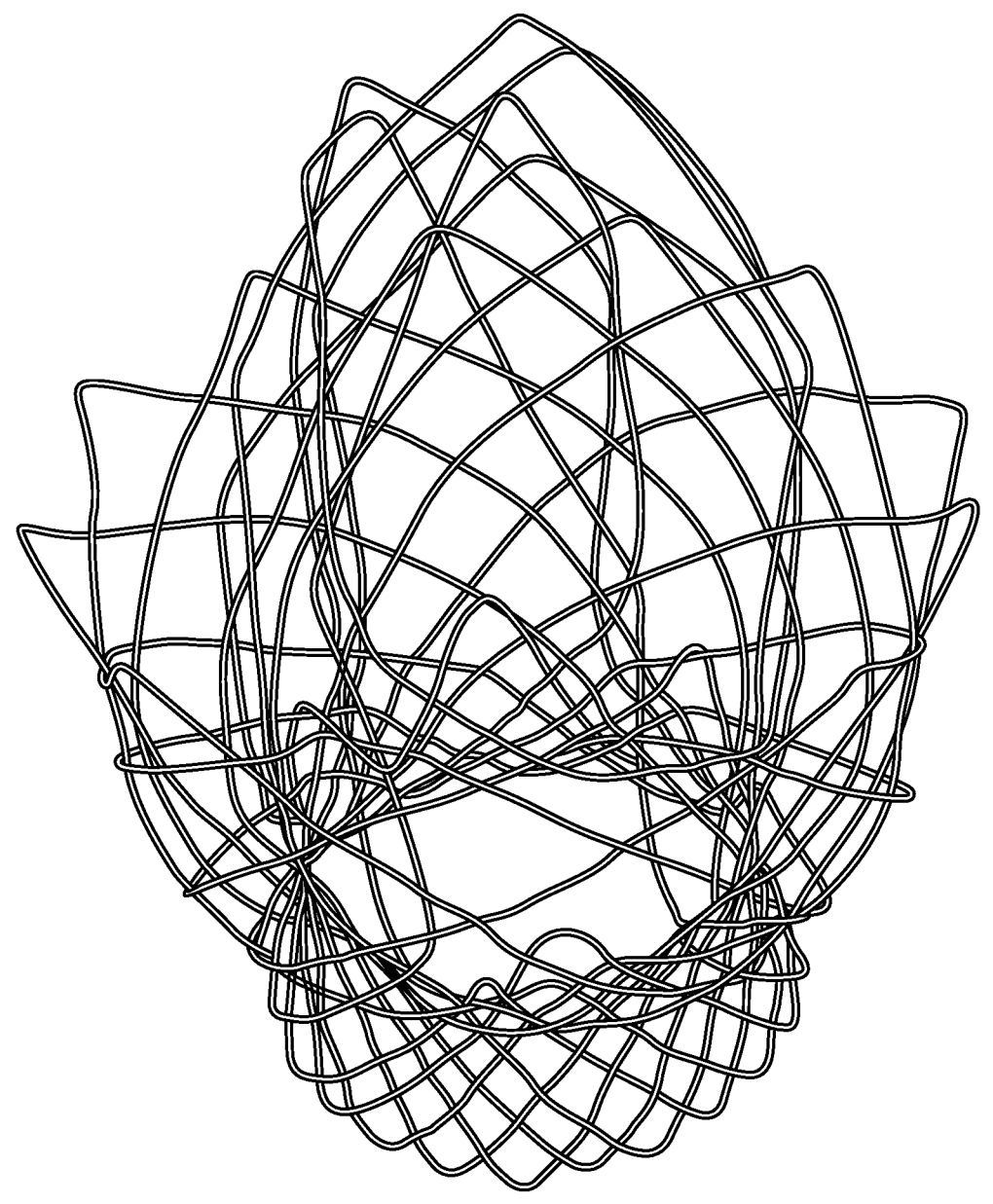

FIG. 15 generally illustrates an embodiment of a heart-valve adapter as disclosed herein.

Figure 16A:
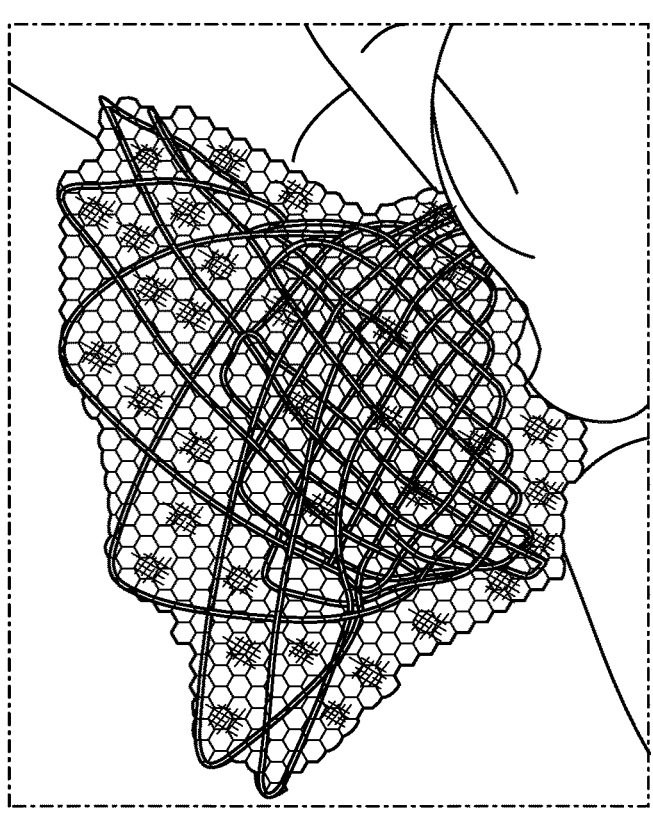
Figure 16B:
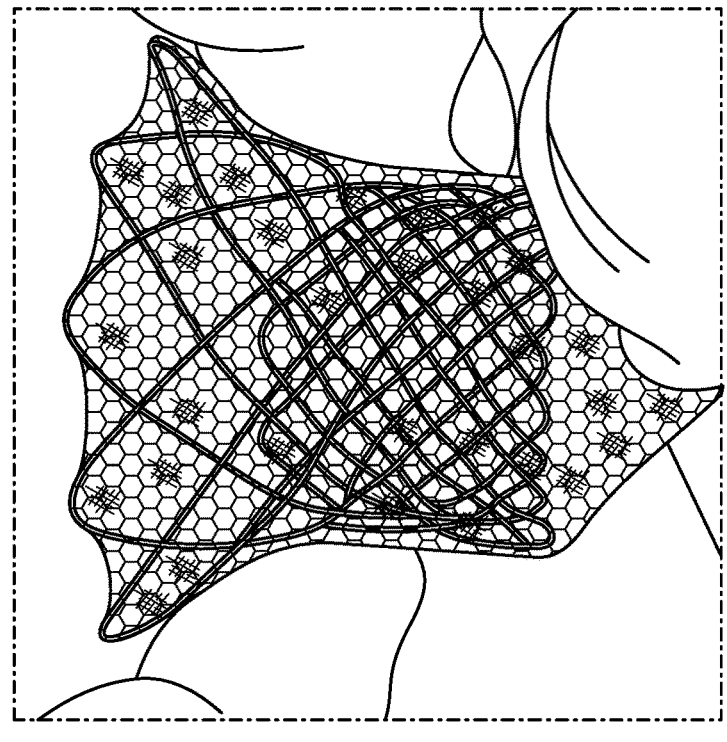

FIGS. 16A and 16B generally illustrate an embodiment of a heart-valve adapter as disclosed herein.

Figure 17A:
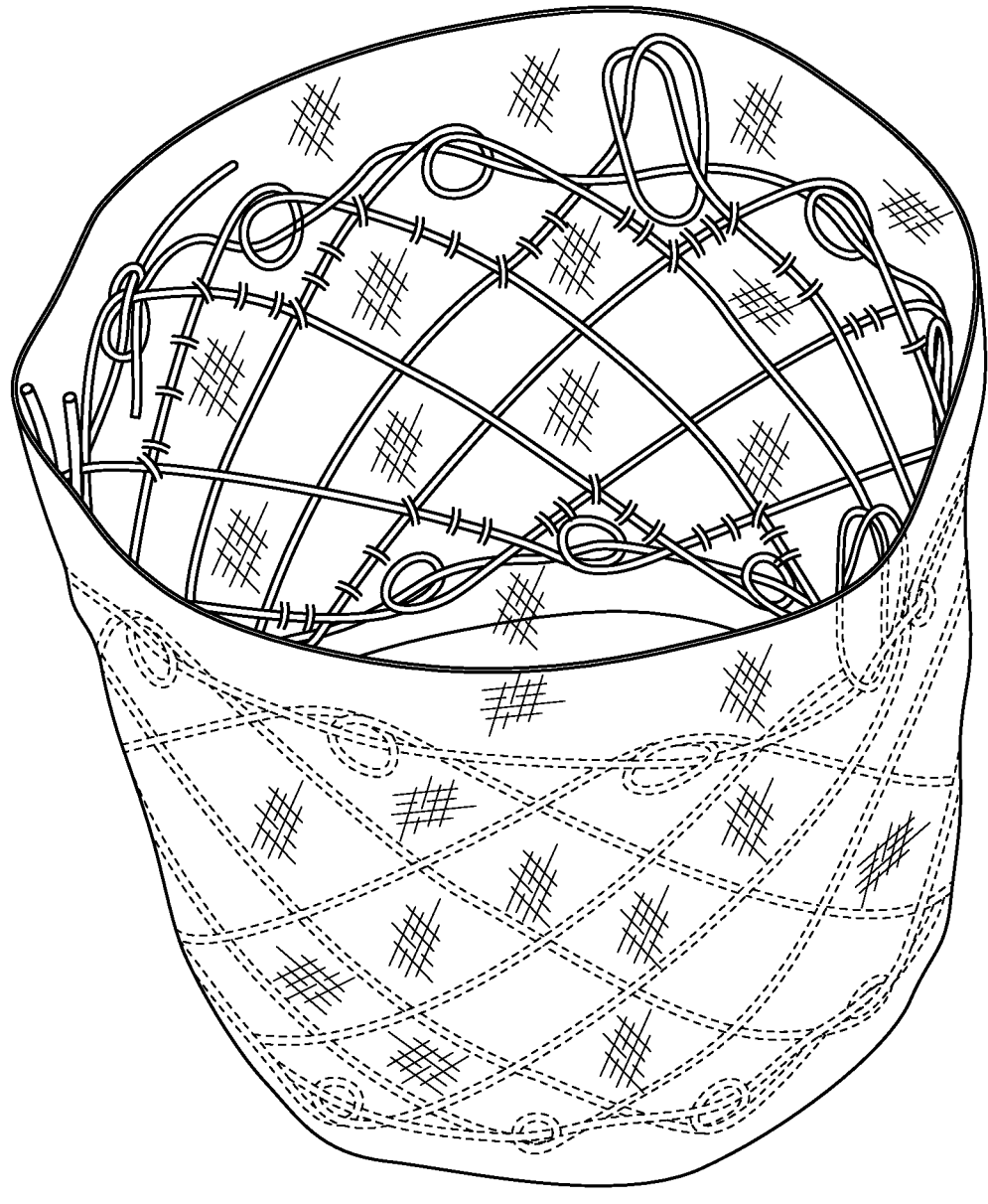
Figure 17B:
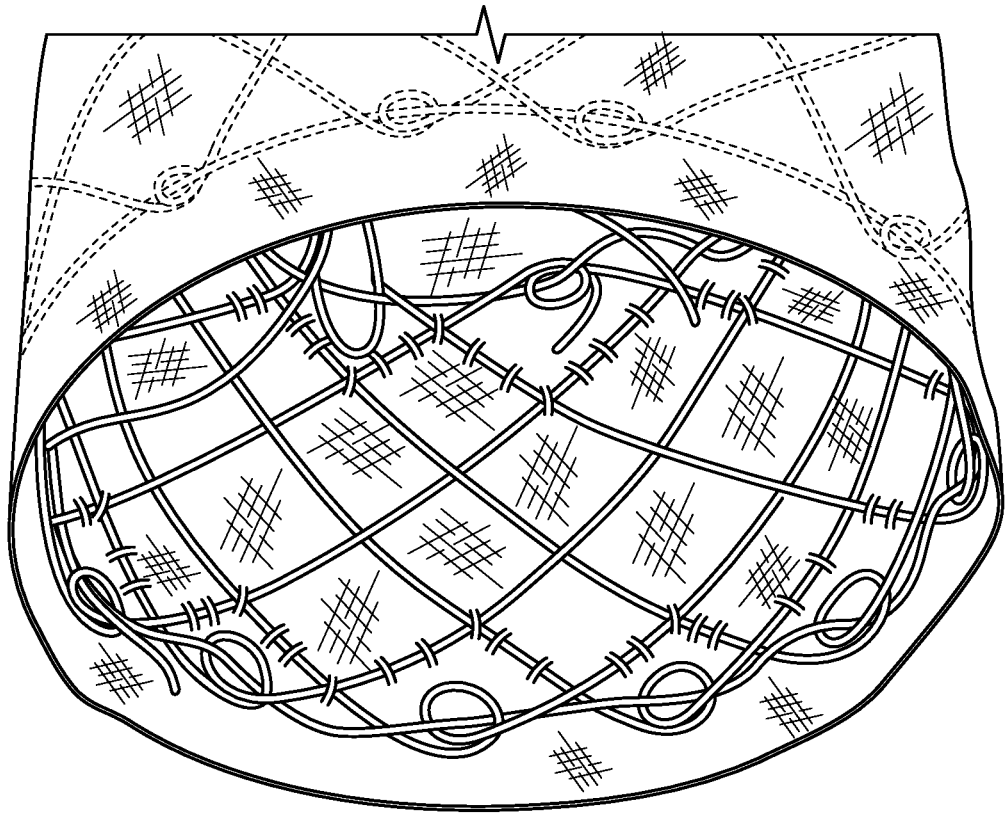

FIGS. 17A and 17B generally illustrate an embodiment of a heart-valve adapter as disclosed herein.

Figure 18:
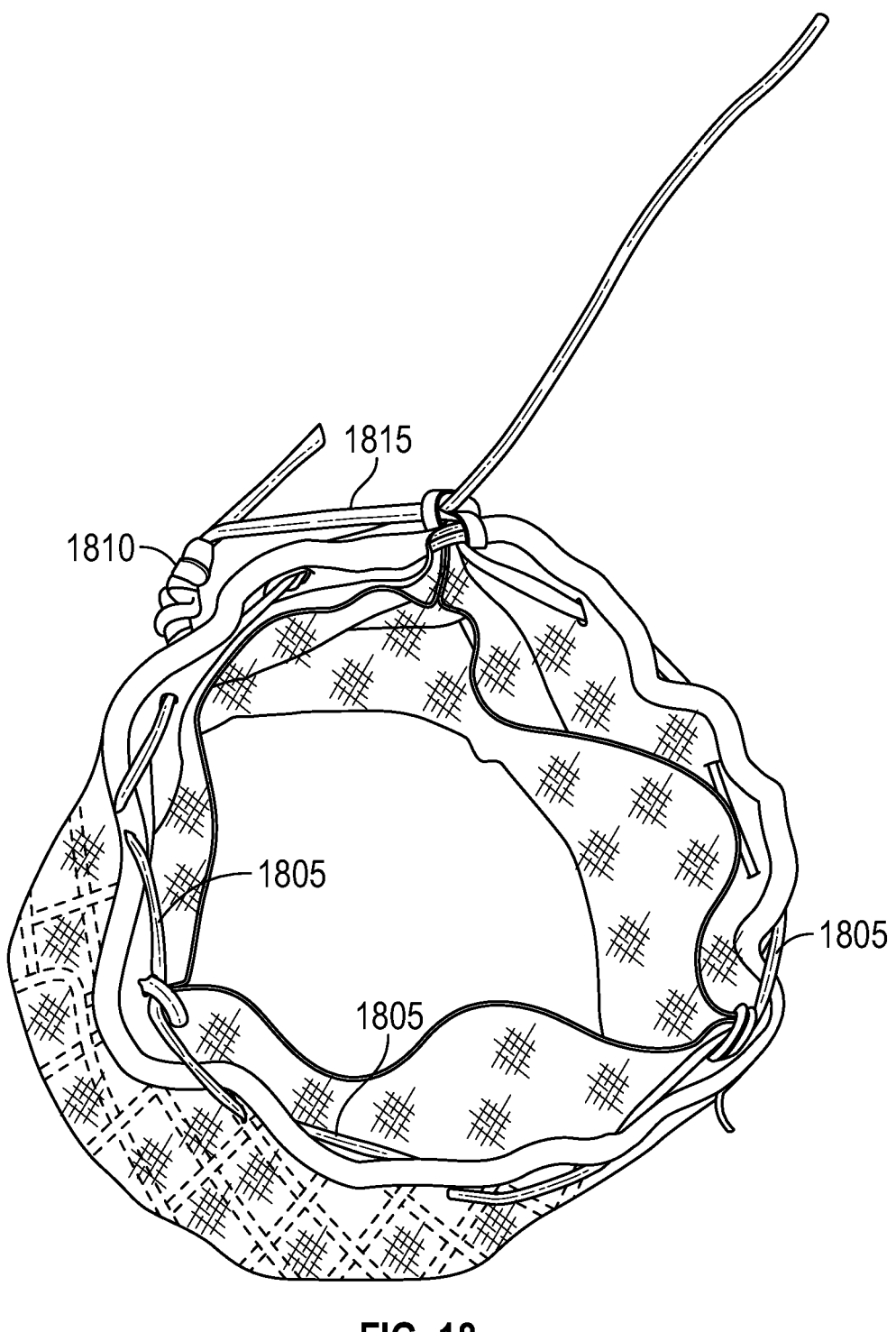

FIG. 18 generally illustrates an embodiment of a heart-valve adapter as disclosed herein.

Figure 19:
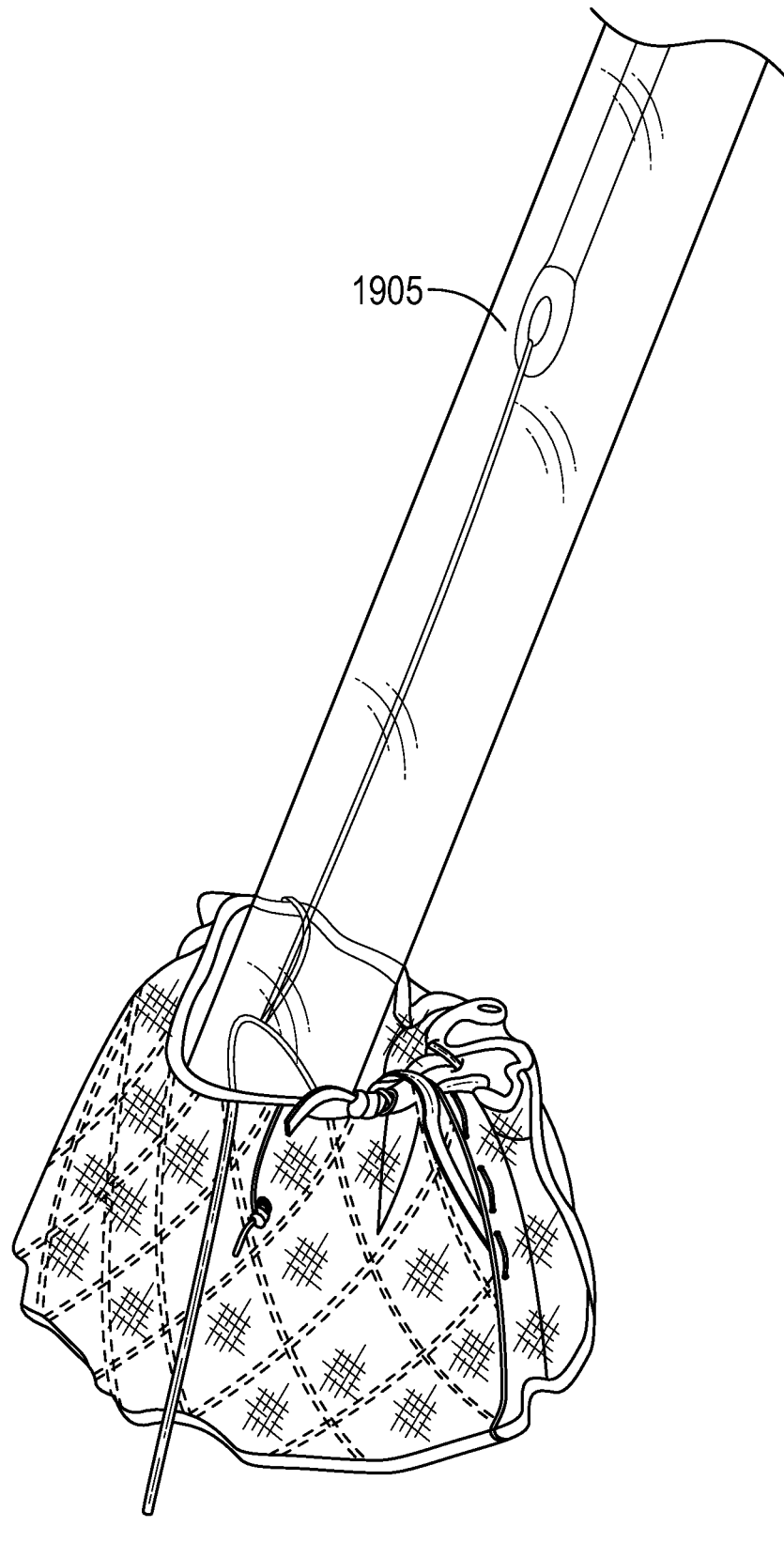

FIG. 19 generally illustrates an embodiment of a heart-valve adapter as disclosed herein.

Figure 20:
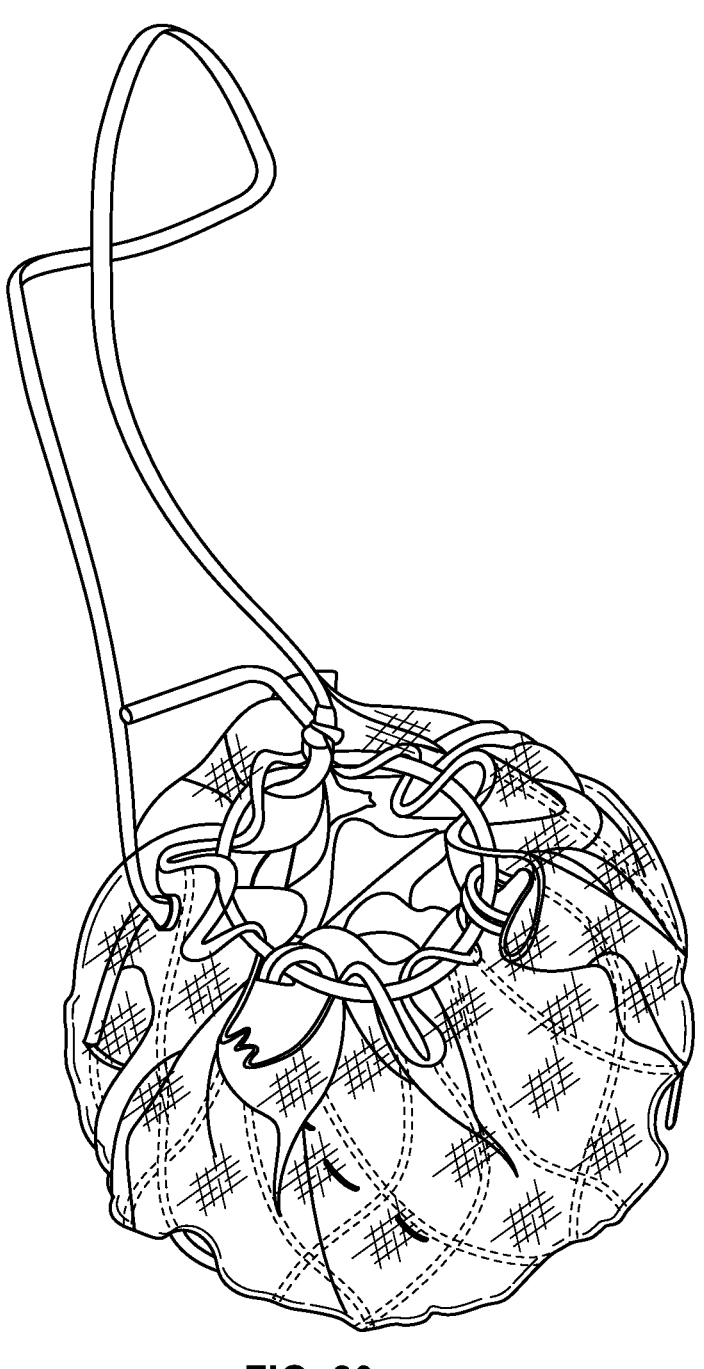

FIG. 20 generally illustrates an embodiment of a heart-valve adapter as disclosed herein.

DETAILED DESCRIPTION OF EMBODIMENTS

Before the present systems and methods are disclosed and described, it is to be understood that the systems and methods are not limited to specific methods, specific components, or to particular implementations. It is also to be understood that the terminology used herein is for the purpose of describing particular embodiments only and is not intended to be limiting. Various embodiments are described with reference to the drawings. In the following description, for purposes of explanation, numerous specific details are set forth in order to provide a thorough understanding of one or more embodiments. It may be evident, however, that the various embodiments may be practiced without these specific details. In other instances, well-known structures and devices are shown in block diagram form to facilitate describing these embodiments.

Disclosed herein are devices, systems, and methods for providing a lower-profile heart-valve adapter while simultaneously increasing the stiffness and strength of anchoring/stabilizing elements. Further disclosed is a heart-valve adapter (referred to herein as the "Adapter" solely for ease of use) comprising at least a collapsible adapter-body and sealing-skirt assembly that together serve to provide a sealing portion. The disclosure and corresponding concepts described herein as applied to treatment of mitral valve pathologies may similarly be applied to treatment of the aortic valve as well as the tricuspid and pulmonary valves.

The Adapter may be delivered through a catheter and easily controlled and securely deployed via common catheter guidance techniques. The Adapter may comprise leaflet-engagement attachments, such as anchoring appendages, for the purpose of securing to native valve leaflets. For example, the Adapter may be placed in proximity to posterior leaflets with securement and anchoring features extending and positioned anywhere from 120 to 180 degrees apart, a preferred embodiment of a 150-degree span. The Adapter may further comprise attachments and additional features for catheter delivery, positioning and partial deployment, and retrieval.

Figure 1:
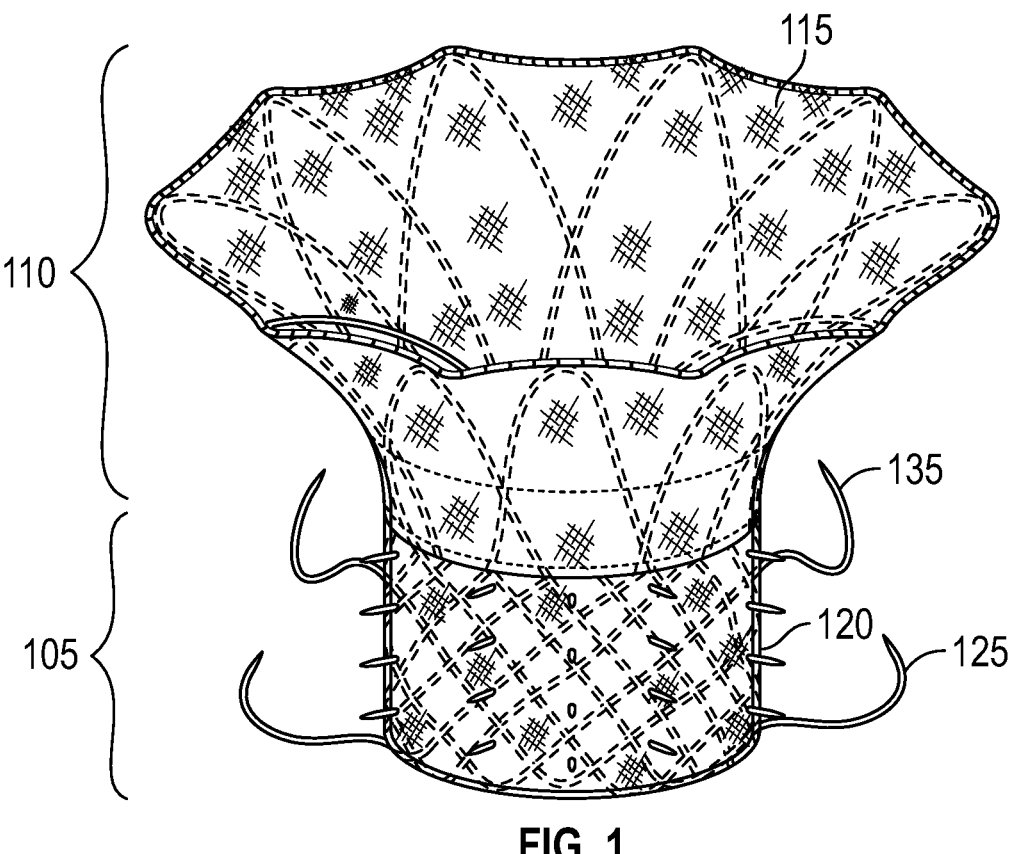
FIG. 1 generally illustrates an embodiment of a heart-valve adapter as disclosed herein.

FIG. 1 generally illustrates an embodiment of a heart-valve adapter as disclosed herein. In an embodiment, as shown in FIG. 1, the Adapter is a tubular braided frame comprising at least a body 105 portion with an inflow end and an outflow end. The Adapter may further comprise an atrial sealing skirt 110 portion that, in some embodiments, extends out from the inflow end of the tubular braided frame. The adapter body 105 and sealing skirt 110 may be constructed of varying material and vary in dimensions. For example, the adapter body 105 and sealing skirt 110 may be made up of a wire braid of one or more wires with different diameters, wherein the wires extend out as flanges away from the body 105 portion, and wherein the extended flanges making up the sealing skirt 110. The wire may be made of material such as nitinol and designed to be compressed to a small diameter—such as 4 mm to 6 mm—to be delivered in a catheter. When released, the adapter body 105 and sealing skirt 110 may expand in size (i.e. the body expanding to 25 mm or greater in diameter and the sealing skirt expanding anywhere from 40 mm to 70 mm in diameter). Other materials from which the wire may be made include but are not limited to stainless steel, cobalt chrome, and nylon.

The adapter body 105 and sealing skirt 110 may be strategically covered in fabric 115 for the purpose of flow sealing and/or encouraging (e.g. influencing: either promoting or inhibiting) tissue growth after implantation. In other embodiments, the fabric 115 may cover only a portion of the sealing skirt 110 or of the engagement attachments discussed below. The fabric 115 may extend over the inside and outside portions of the tubular braided frame, which may include the body 105, the sealing skirt 110, and/or any engagement attachments.

The exterior surface of the adapter body 105 may also be covered with a multitude of small, short barbs 120 that, in some embodiments, are an extension of the tubular braided frame and extend out from the outflow end to function as an engagement attachment. The barbs 120 may be used to engage the leaflet or annulus of a malfunctioning cardiac valve, such as a mitral valve. The barbs 120 may be made up of basic, short wires and/or may also have an extra barb-component, like a fishhook barb, to fixably retain the annular tissue.

The adapter body 105 may also have one or more hooks 125 or 135 (more or less in number than the barbs 120) varying in size, that can hook under the native valve tissue. These larger hooks may or may not have fishhook-type barbs. The larger hooks may have a spring-like function that engage with the native valve tissue and prevent it from moving. The hooks 125 or 135 may be, in some embodiments, are an extension of the tubular braided frame and extend out from the outflow end to function as an engagement attachment.

In a preferred embodiment, the sealing skirt 110 may be connected to a catheter, wherein the Adapter is sequentially released from the catheter once the adapter body 105 is released and engaged with annual tissue. The sealing skirt 110 may be designed to flex downward, toward, or even past the plane defining the joint between the adapter body 105 and the sealing skirt 110. The multitude of barbs 120 on the adapter body 105 work together to ensure the adapter body 105 is strongly engaged in the native annulus and resists the downward pressure of the sealing skirt 110, such that the sealing skirt 110 creates a strong seal against the atrial tissue surrounding the native valve annulus.

Figure 2:
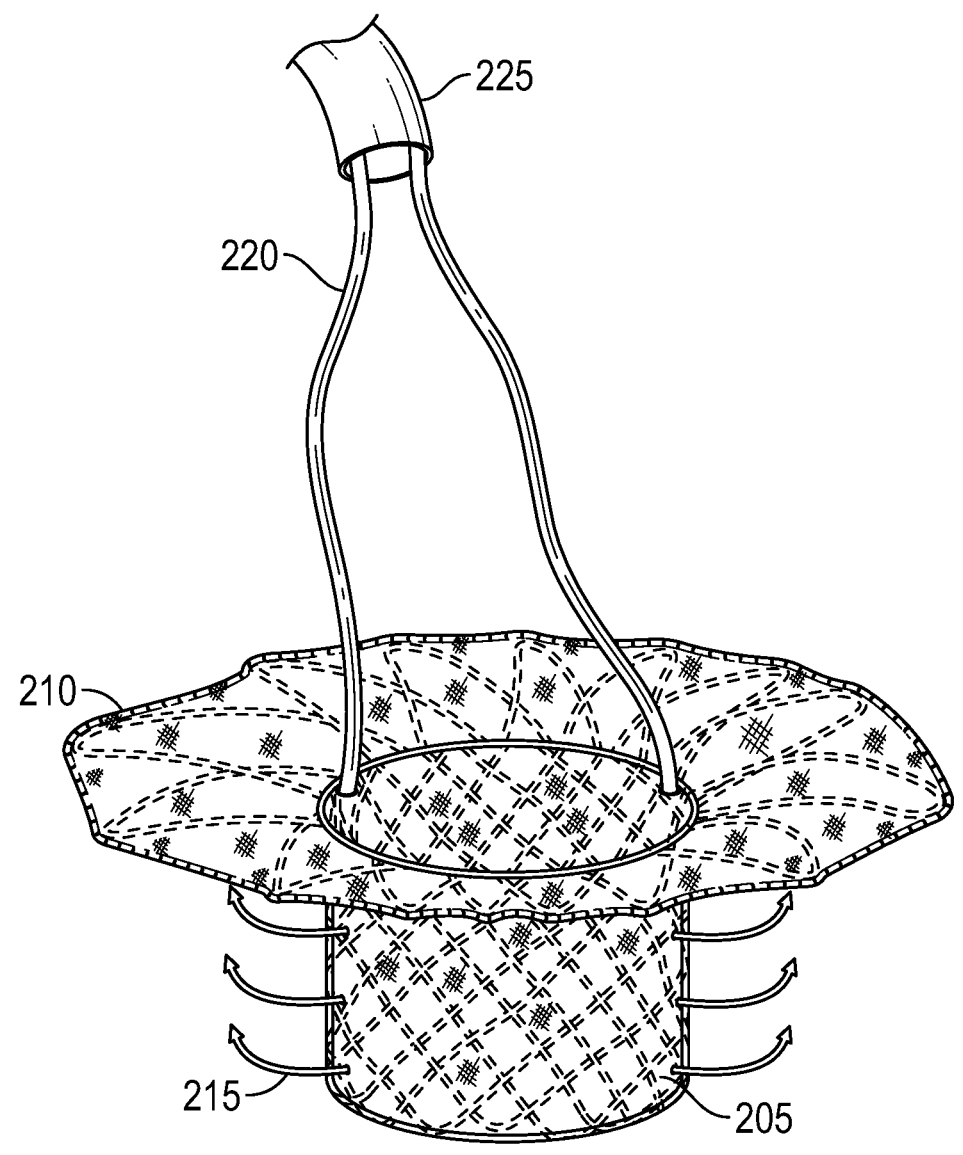
FIG. 2 generally illustrates an embodiment of a heart-valve adapter as disclosed herein.

FIG. 2 generally illustrates an embodiment of a heart-valve adapter as disclosed herein. As shown in FIG. 2, an Adapter may comprise an adapter body 205 and sealing skirt 210, wherein the sealing skirt 210 has expanded at a point approximately near the plane of the joint between the adapter body 205 and the sealing skirt 210. The Adapter may further comprise barbs 215, which have the ability to be retracted via leashes 220 through a catheter 225. The barbs 215 may fixably grab the native valve leaflets and force them against the adapter body 205. Once the barbs 215 are retracted, the leashes 220 can be removed via the catheter 225.

The Adapter may further comprise anchoring functionalities, which are similar to the engagement attachments disclosed herein. For example, the Adapter may be anchored in the Chordae. In one embodiment, this may be done with a suture deliberately looped behind the leaflet/chordae structure that can be cinched down. In another embodiment, anchoring may be accomplished with a vine-type structure that entangles the chordae in a one-directional, retaining manner; such as with barbs that allow one-way movement.

FIGS. 3A-3D generally illustrate an embodiment of a heart-valve adapter as disclosed herein. In these figures, the sealing skirt is not shown for ease of illustration. As shown in FIG. 3A, the adapter body 305 is designed with a braid of varying weave densities and/or wire diameters, and/or combined with releasable mechanisms such that the adapter body initially has a round cross-section. The adapter body 305 has barbs 310 designed to engage a native valve leaflet 350. Once the barbs 310 are engaged, the anchoring/attaching functionalities of the Adapter cause it to conform to a "D-shape" or other asymmetrical shape—keeping the receiver body 305 cylindrical or otherwise specifically shaped to receive the valve structure. This accommodation and conformity is achieved via the different weave, wire diameters, or mechanism enabling such. As shown in FIG. 3B, the change in shape creates a sharper curve radius to make the D-shape. The change from a circular cross-section to a D-shape cross-section may pull the leaflet, which can be useful, for example, in a mitral valve where an implant such as the adapter body may cause outflow tract obstruction. FIGS. 3C and 3D disclose an oblique view of the structure and mechanism corresponding with FIGS. 3A and 3B. Embodiments disclosed in FIGS. 3A-3D may also comprise the sealing skirt and other features described in previous drawings.

Figure 4:
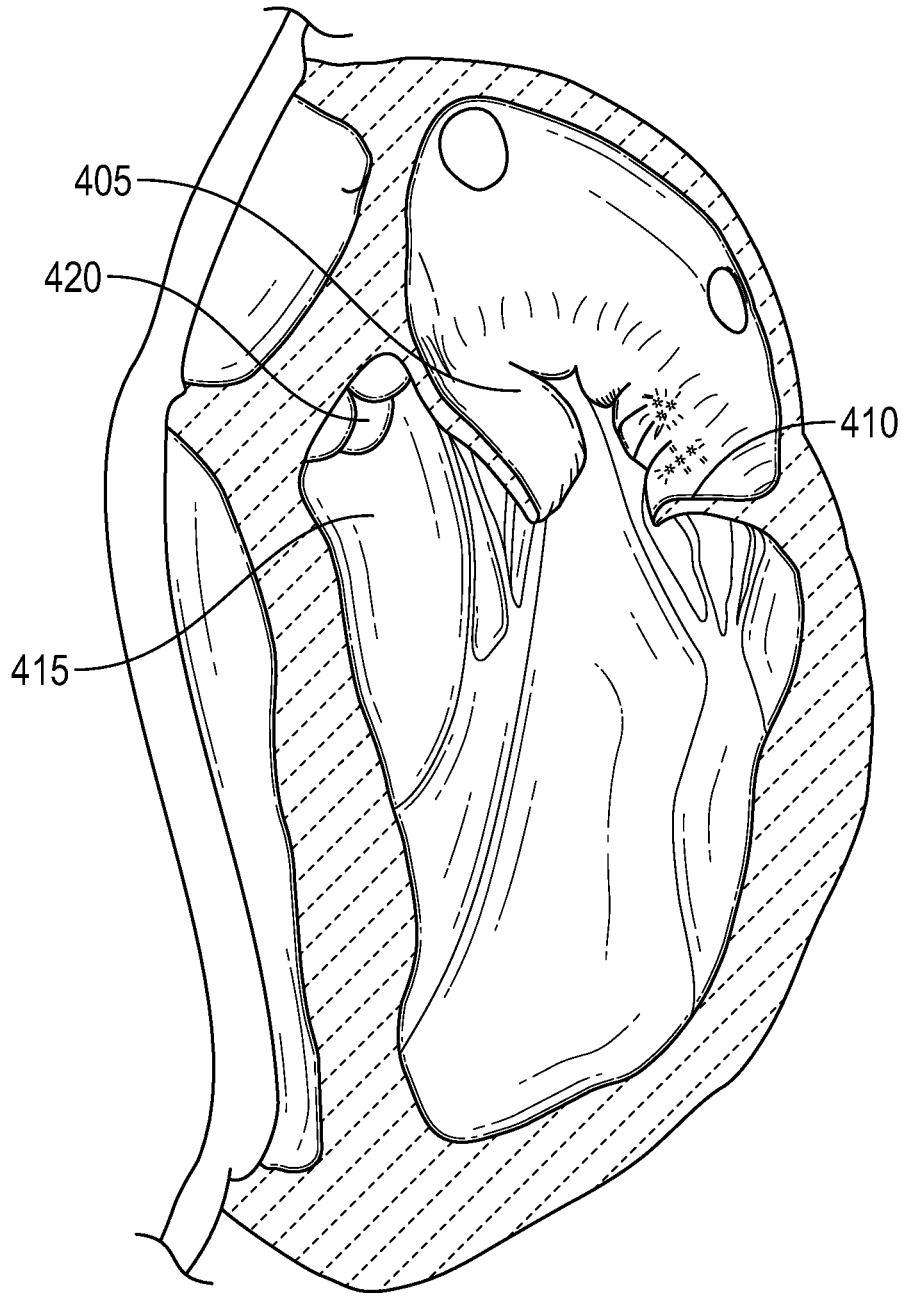
FIG. 4 generally illustrates an embodiment of a heart-valve adapter as disclosed herein.

FIG. 4 generally illustrates an embodiment of a heart-valve adapter as disclosed herein. FIG. 4 discloses a cross-section of the left side of a heart—specifically, a mitral valve that has an anterior leaflet 405, a posterior leaflet 410, and the space to the left of the anterior leaflet called the left ventricular outflow tract (LVOT) 415 that leads to the aortic valve 420. FIG. 4 serves to detail embodiments disclosed in the following Figures.

FIG. 5 generally illustrates an embodiment of a heart-valve adapter as disclosed herein. FIG. 5 discloses an embodiment of the Adapter implanted in a malfunctioning mitral valve, with the adapter body 505 deployed in the mitral valve and the sealing skirt 510 deployed against the floor of the left atrium. In this embodiment, the adapter body 505 is oriented at a slight angle (i.e. from 10-30 degrees relative to the plane of the skirt), such that when deployed, the adapter body 505 is biased towards the posterior leaflet 515.

Deployment as disclosed in FIG. 5 ensures good engagement of barbs into the posterior leaflet but not necessarily the anterior leaflet. The system can be designed to normally be in this geometric condition but be mechanically expandable by design so that it can expand to engage the anterior leaflet, then released back to the normal position after the barbs and/or hooks engage the anterior leaflet. This forces the anterior leaflet towards the posterior leaflet and away from the LVOT, ensuring it is not obstructed post procedure. Also shown are the delivery catheter 520 and a guidewire 525.

FIG. 6 generally illustrates an embodiment of a heart-valve adapter as disclosed herein. FIG. 6 discloses an embodiment wherein the adapter body 605 is configured in a D-shaped cross-section per the disclosure in FIGS. 3A-3D.

FIG. 7 generally illustrates an embodiment of a heart-valve adapter as disclosed herein. As shown in FIG. 7, an embodiment of the Adapter may be mechanically expanded post-implantation and force engagement of the anterior leaflet or other anchoring mechanism using a balloon catheter. Such a balloon-catheter approach is common to valve and vessel stenting procedures and are known in the field. Other methods of temporary mechanical expansion of the adapter body comprise, but are not limited to, cinching mechanisms and pre-sprung wires or the like, which can be pulled or triggered and subsequently released.

In another embodiment, the adapter body may be used to engage the leaflets with the barbs, wherein the body expands to a diameter larger than the diameter at deployment to ensure engagement with the leaflets. As the device is further deployed, the diameter of the engaged portion reduces to a final configuration—symmetrical or asymmetrical—thereby pulling the leaflets towards the device and away from the LVOT.

FIG. 8 generally illustrates an embodiment of a heart-valve adapter as disclosed herein. FIG. 8 discloses a final configuration of an adapter in its original position after release, wherein the anterior leaflet is drawn and held towards the posterior leaflet, ensuring no obstruction of the LVOT.

FIG. 9A generally illustrates an embodiment of a heart-valve adapter as disclosed herein. FIG. 9 discloses the wire braid frame making up the Adapter. As further shown in FIG. 9, the wire braid frame may comprise a 24-point braid pattern, with double posterior leaflet anchors 905, wherein the double posterior leaflet anchors 905 are used to maintain symmetry and additionally provide twice the structural anchoring. The wire braid frame may also comprise dual stabilization anchors 910. Also shown is that the wire braid frame may have the anchor locations available in 15-degree increments. The anchors may be, in some embodiments, an extension of the tubular braided frame and extend out from the outflow end to function as an engagement attachment In other embodiments, the wire braid frame of an Adapter may have anchors—or barbs, hooks, or clips, as disclosed herein—that are grafted on. For example, FIG. 9A shows the combination of a larger gage wire (0.0175"-0.02") (represented by the stabilization anchors 910) and smaller gage wire (0.012-0.0175") (represented by the posterior leaflet anchors 905 and further represented by additional wires 915) by means of a joining operation at the interface between the varying-size wires. The connection interface may be a weld or a weld with a support tube.

FIG. 9B generally illustrates an embodiment of a heart-valve adapter as disclosed herein. As shown in FIG. 9B, the stabilization anchors 910 may be shape set to contain a second bend on the end of the U-shape. In other embodiments, the stabilization anchors are disposed symmetric to the P2 anchors with a span of 150 degrees. At this angle, the stabilizing anchors optimally insert behind the posterior leaflets, extending to the mitral annulus near the fibrous trigones.

FIG. 9C generally illustrates an embodiment of a heart-valve adapter as disclosed herein. As shown in FIG. 9C, a wire braid frame may comprise posterior leaflet anchors 905 but no stabilization anchors. In this embodiment, the posterior leaflet anchors 905 and flange 920 provide the required securement of the implant and anchoring to the native annulus. In other embodiments, a single quadruple anchor designated as a P4 anchor could provide even more structural anchoring by extending four loops instead of only two. (P4 refers to a four-humped anchor in the location of the P2 anchors currently. The number and locations of these anchors may fall anywhere within the 180-degree span of the aforementioned anchoring features.) And additional anchors and/or leaflet clips can augment the posterior leaflet anchors.

Figure 10A:
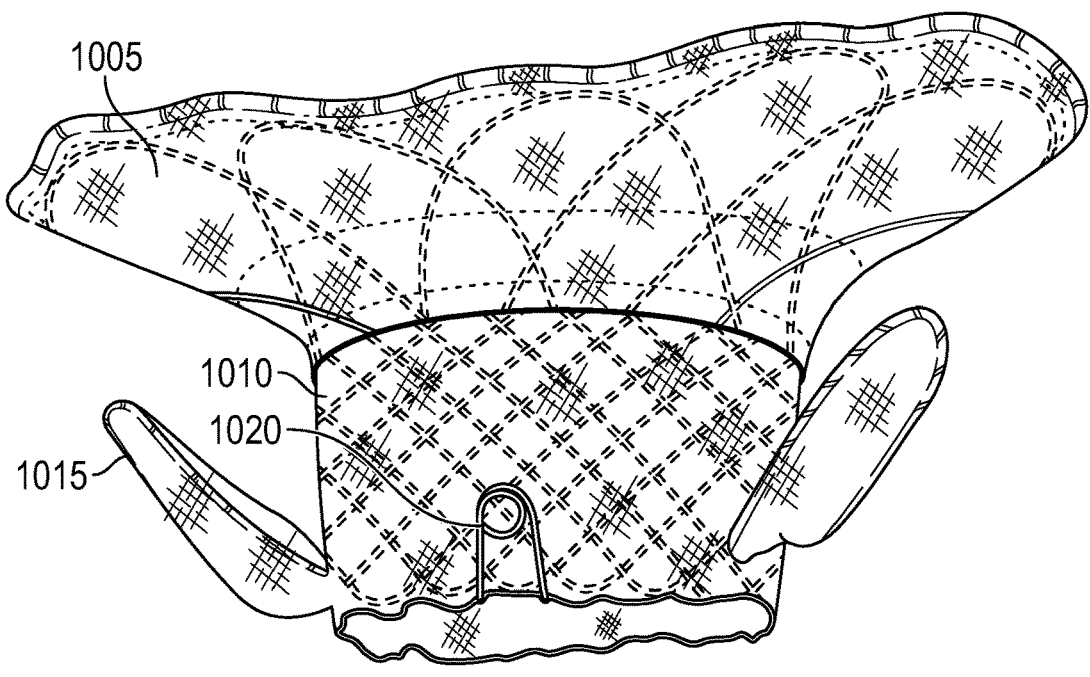

FIGS. 10A-10E generally illustrate an embodiment of a heart-valve adapter as disclosed herein. In one embodiment, as shown in FIG. 10A, an Adapter may comprise an atrial sealing skirt 1005, an adapter body 1010, and a stabilization anchor 1015 that are all covered in a fabric for the purpose of flow sealing and/or encouraging (e.g. influencing: either promoting or inhibiting) tissue growth after implantation. The embodiment may further comprise a clip 1020 that is not covered in a fabric.

Figure 10B:
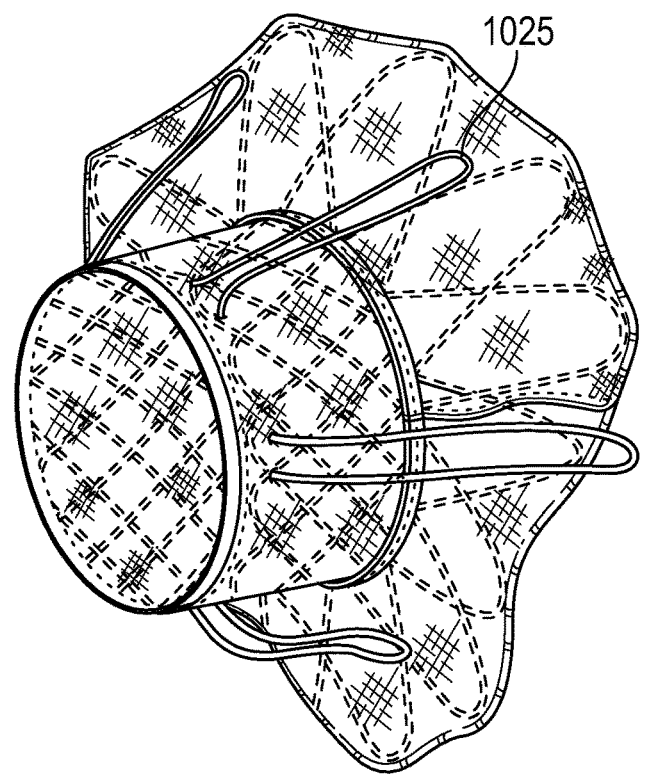
Figure 10C:
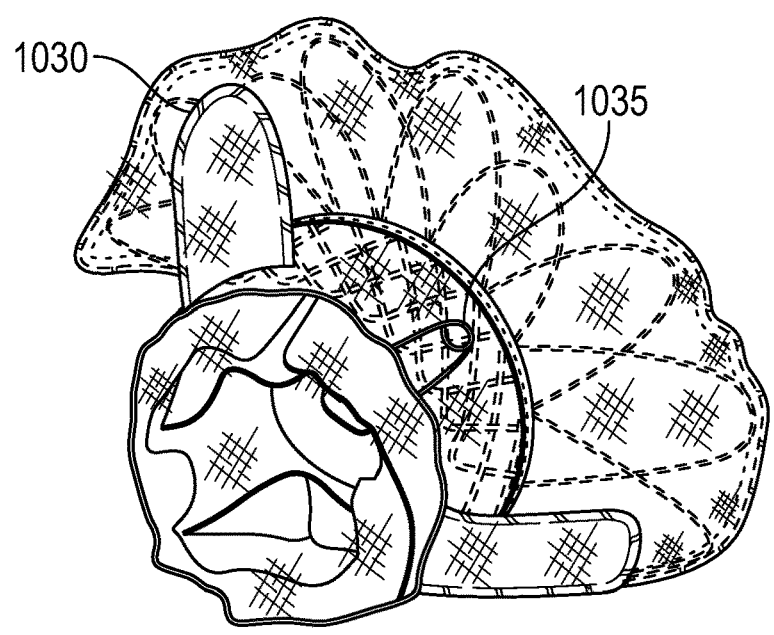

FIGS. 10B and 10C show embodiments of an Adapter. FIG. 10B shows an Adapter comprising only stabilization anchors 1025, none of which are covered by a fabric. FIG. 10C shows an Adapter comprising posterior leaflet anchors 1030 with a fabric layer and clips 1035.

Figure 10D:
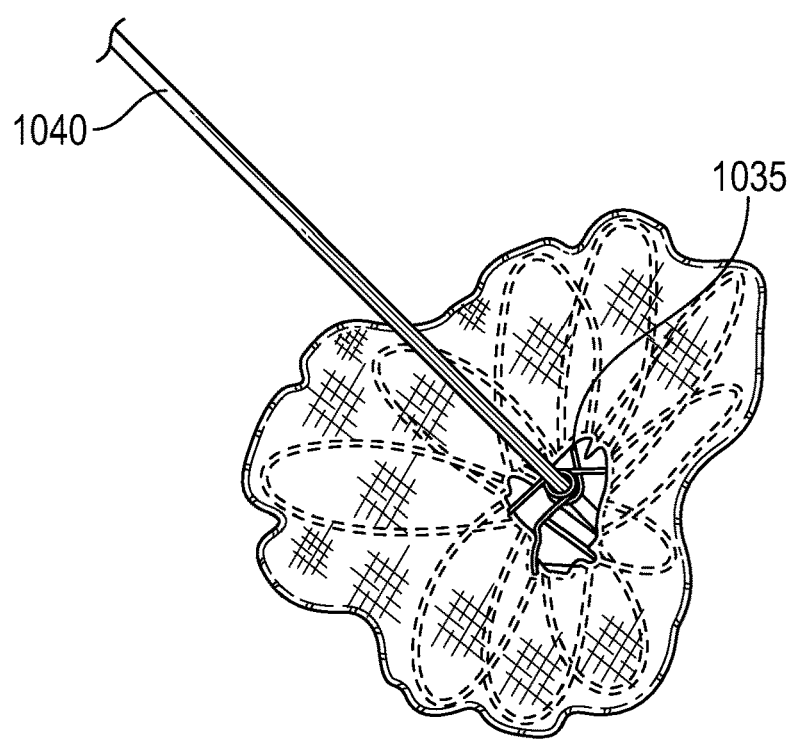
Figure 10E:

FIG. 10D shows an embodiment of an Adapter with a delivery rod 1040 inserted through it. As shown in FIG. 10D, a suture or stiff rod may be thread through the tabs on the inflow end of an Adapter and used to constrain the implant to an intermediate-compressed state. FIG. 10E shows an embodiment of the bottom of the Adapter shown in FIG. 10E.

FIGS. 11A-11C generally illustrate an embodiment of a heart-valve adapter as disclosed herein. These figures show an embodiment of an Adapter comprising a clip component for the purpose of improving delivery control, via secure attachment of the Adapter to a delivery catheter, and for the purpose of improving the efficiency and efficacy of leaflet attachment.

FIG. 11A shows a flat-pattern schematic of a wire frame of an Adapter with a clip 1105, wherein the clip 1105 may be a looped portion of the wire frame extending out from the main body of the wire frame. In some embodiments, a clip 1105 may be positioned at two or more separate locations around the circumference of the Adapter. In other embodiments, clips 1105 be shape set 180 degrees such that they can provide for a hook shape to clip onto the native valve leaflets. For example, once an Adapter is released from a delivery system, the clips 1105 may attach onto the native valve leaflets, providing securement of the Adapter.

FIG. 11B shows an embodiment of the wire frame of an Adapter with clips 1105, posterior leaflet anchors 1110, and flanges 1115. FIG. 11C shows an embodiment of clips 1105 the wire frame of an Adapter with clips 1105, posterior leaflet anchors 1110, and flanges 1115. In varying embodiments, some or all of the engagement attachments—anchors, barbs, hooks, and clips—may have a layer of material covering them.

The anchors and clips disclosed herein further serve the purpose of improving control and retrieval of the Adapter. For example, the anchors and clips may be controlled—e.g., partially or fully retracting them—by attaching sutures or other cord-type control features to the anchors and/or clips and then running the line through the frame of the Adapter.

In an embodiment of collapsible anchors, a cord is stitched through the tips of the anchors 5-7 times and the excess cinches with a figure-eight knot. Then the two ends of the cord are wrapped through the inside of the Adapter and are pulled into the existing holes in the flange out through the bottom. Leaving 4 mm of excess cord, the ends are tied off with two square knots and the ends are snipped off. These secured sutures become pull tabs that can be grabbed with forceps and pull away to collapse the anchors or clips using a perpendicular force.

In an embodiment of collapsible flanges, a cord is looped through the existing holes in the flange, leaving a diamond-shaped pattern facing the top of the Adapter. The two ends of the cord are tied together with two square knots, creating a closed loop. This is to allow forceps to grab the cord and collapse the flange. In other, embodiments, both the anchors/clips and flange are simultaneously collapsed, thus further improving the ability to remove the Adapter.

Additionally, the collapsible anchors and flanges may enable and improve the ability control the anchors/clips and flanges during deployment of the Adapter. For example, by looping cord through the loops left by the pull tabs, the anchors may be controlled by collapsing one or both from the base of a delivery device, such as a catheter. This is useful when delivering the Adapter, allowing the physician the ability to control more accurately the placement and positioning of the anchoring/stabilizing elements.

FIGS. 12A and 12B generally illustrate an embodiment of a heart-valve adapter as disclosed herein. FIG. 12A shows a top view of an Adapter and FIG. 12B shows a bottom view of an Adapter. As shown in FIGS. 12A and 12B, the inflow end of an Adapter may comprise anchor retracting chords coming through the flow portion and anchor to the underside of a flange. These sutures permit control of the anchors by pulling and releasing the chords. Alternatively, the sutures may be releasably attached to a delivery system to provide similar manipulation of the anchors. FIG. 12B further discloses the chords attached to the anchors.

FIGS. 13A-13C generally illustrate an embodiment of a heart-valve adapter as disclosed herein. FIGS. 13A-13C show attachment configurations for a collapsible flange. FIG. 13C shows how, in one embodiment, sutures extendings from a delivery system are connected to points on the Adapter, allowing for control for repositioning and/or orientation of the flange during deployment.

FIGS. 14A-14D generally illustrate an embodiment of a heart-valve adapter as disclosed herein. FIGS. 14A-14D show the attachment configurations for collapsible anchors and clips and further disclose a close-up view of a suture pattern that is used to collapse and control the anchors from all angles of the Adapter. In these embodiments, a delivery component, such as one comprising one or more suture lines, is connected on a first to the engagement attachment, wherein the one or more suture lines connects on a second end to a controlling mechanism.

FIG. 15 generally illustrates an embodiment of a heart-valve adapter as disclosed herein. As shown in FIG. 9, an embodiment of the Adapter may comprise a shape and structure that supports the structure of the sinus of Valsalva. Such a structure ensures patency of the coronary arteries and can enhance coronary perfusion either by mimicking the natural valve function or by adding additional hemodynamic responsive members, such as leaflet-like cusps on the proximal portion of the device.

As disclosed herein and corresponding with FIG. 9, the compliant nature of the frame and the inherent accommodation of non-symmetrical anatomy lends itself to an unmet need for a device that can be used in the aortic valve position when balloon expansion of calcified tissue yields an orifice of asymmetrical geometry.

FIGS. 16A and 16B generally illustrate an embodiment of a heart-valve adapter as disclosed herein. As shown in FIGS. 16A and 16B, an embodiment of the Adapter may comprise a continuous piece of material around the outside of an Adapter frame. A continuous seal extending from an adapter skirt may be configured from the material (such as fabric) extending from an inflow edge of a receiver portion of the Adapter to the extrados of a receiver body. A strip of ingrowth fabric can be sewn around the inflow edge of the skirt, with a non-porous coating forming a continuous seal extending into the ventricle.

The continuous surface of the fabric may be locally influenced and characterized for modulating or even contradicting properties, such as coating with medical polymer in locations where no tissue attachment is desired, hydrogels where space-filling or latent actions are desired, or a hydrophilic tissue adhesive. The continuous material structure of the fabric may be voluminous in nature, filling space and adapting the round heart valve to the asymmetrical shape of the valve annulus. Combined with other attachment methods, an embodiment of the mitral-valve adapter fabricated with this method aids in engagement and attachment of the leaflet tissue and other sub-valvular structures. The partially porous fabric provides an improved seal for a replacement valve, enabling accommodation to irregular shaped anatomy through the compliance of the fabric.

FIGS. 17A and 17B generally illustrate an embodiment of heart-valve adapter as disclosed herein. As shown in FIGS. 17A and 17B, an embodiment of the Adapter may be fabricated using a constraint to hold a mitral-valve adapter frame at a specific dimension while attaching material to influence device performance. A fabrication technique is disclosed, which acts to influence the disposition of a braided wire frame—removing the inherent freedom of movement and unpredictability that is present between relative members of the frame structure when in a load-free state. This technique involves restraining the radial expansion of the frame with a constraint, such as feeding some number of sutures through or around the structure to hold it at a specific dimension other than its unrestrained, "free" dimension. In subsequent fabrication steps, the structure is incorporated into an assembly that adopts this new configuration and considers this to be the final dimension. When the constraints are removed from the braided frame, this braided frame tries to recover to its original "free" dimension—applying additional radial force to the surrounding structure while being constrained to the desired dimension.

In some embodiments, the tubular braided frame of the Adapter may be a braid of one or more wires, wherein the braid of the one or more wires is a zig-zag braid, or an over-under braid.

FIG. 18 generally illustrates an embodiment of a heart-valve adapter as disclosed herein. As shown in FIG. 18, a drawstring 1805 may be included with a slip knot 1810 that cinches to facilitate removal of the valve portion. FIG. 18 shows a drawstring 1805 for constricting the outflow end of a collapsible valve Adapter constructed from a cinching slip knot and tethered segment 1815, similar to a hangman's knot with the noose encircling the outflow end of the valve through the loops. The long end extending from the knot may be tethered to a commissure post creating a hookable portion of exposed suture material. Radiopaque markers can be placed on either end of the tether to help guide the hooking instrument to the tether FIG. 19 generally illustrates an embodiment of a heart-valve adapter as disclosed herein. As shown in FIG. 19, an additional cylindrical tube 1905 can be used to provide countertraction to allow tightening of the cinching slip knot. Increased tension/countertraction will result in the valve end collapsing irreversibly due to the friction in the knot. Thus the valve can be drawn down and removed from the body more easily and safely.

FIG. 20 generally illustrates an embodiment of a heart-valve adapter as disclosed herein. More specifically, FIG. 20 shows a partially compressed valve after the drawstring has been tightened.

The degree of radial force transmitted to the fabric material from the frame can be adjusted as required to achieve the optimal combination or performance properties. In particular, the strain energy density of the structure can be more uniform. A greater stiffness is achieved (resulting in a better seal) with less material, resulting in a more low-profile structure. The suture finally provides a biasing of the structure toward a desirable diameter and height for the valve structure.

To expand the concept further, structures that possess features described herein may be co-deployed singularly or with a connected design, so as to engage both the mitral and the aortic valve apparatus and/or annulus. The intent is to influence the leaflets of both valves, as well as the angulation of the valves relative to one another, to ensure the most effective management of flow through the ventricle and maximizing the efficiency of the Outflow Tract.

Other embodiments may include combinations and sub-combinations of features described or shown in the several figures, including for example, embodiments that are equivalent to providing or applying a feature in a different order than in a described embodiment, extracting an individual feature from one embodiment and inserting such feature into another embodiment; removing one or more features from an embodiment; or both removing one or more features from an embodiment and adding one or more features extracted from one or more other embodiments, while providing the advantages of the features incorporated in such combinations and sub-combinations. As used in this paragraph, "feature" or "features" can refer to structures and/or functions of an apparatus, article of manufacture or system, and/or the steps, acts, or modalities of a method.

References throughout this specification to "one embodiment," "an embodiment," "an example embodiment," etc., indicate that the embodiment described may include a particular feature, structure, or characteristic, but every embodiment may not necessarily include that particular feature, structure, or characteristic. Moreover, such phrases are not necessarily referring to the same embodiment. Further, when a particular feature, structure, or characteristic is described in connection with one embodiment, it will be within the knowledge of one skilled in the art to affect such feature, structure, or characteristic in connection with other embodiments whether or not explicitly described.

Unless the context clearly indicates otherwise (1) the word "and" indicates the conjunctive; (2) the word "or" indicates the disjunctive; (3) when the article is phrased in the disjunctive, followed by the words "or both," both the conjunctive and disjunctive are intended; and (4) the word "and" or "or" between the last two items in a series applies to the entire series.

Where a group is expressed using the term "one or more" followed by a plural noun, any further use of that noun to refer to one or more members of the group shall indicate both the singular and the plural form of the noun. For example, a group expressed as having "one or more members" followed by a reference to "the members" of the group shall mean "the member" if there is only one member of the group.

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

What is claimed:

1. An implantable heart-valve adapter apparatus, comprising:

a tubular braided frame, wherein the tubular braided frame comprises an inflow end and an outflow end;

wherein the tubular braided frame extends out from the inflow end to form at least one flange; and wherein the tubular braided frame extends out from the outflow end to form engagement attachments comprising a leaflet clip and two U-shaped stabilization anchors, wherein the engagement attachments are integrally formed with the tubular braided frame as a single component, wherein the leaflet clip is disposed between the two U-shaped stabilization anchors, wherein when deployed in a native mitral valve comprising a native mitral annulus and one or more native leaflets, the leaflet clip engages behind the one or more native leaflets and the two U-shaped stabilization anchors extend towards the native mitral annulus behind the one or more native leaflets.

2. The apparatus of claim 1, wherein the tubular braided frame is constructed of one or more material that is expandable or compressible or both expandable and compressible.

3. The apparatus of claim 2, wherein the apparatus comprises a layer of material extending over an outside portion and inside portion of the tubular braided frame, the at least one flange, and the engagement attachments.

4. The apparatus of claim 2, wherein the apparatus comprises a layer of material extending over an outside and inside portion of the tubular braided frame and the at least one flange.

5. The apparatus of claim 2, wherein the stabilization anchors are between 120 to 180 degrees apart.

6. The apparatus of claim 2, wherein the tubular braided frame is a braid of one or more wires, wherein the braid of the one or more wires is either a zig-zag braid or an over-under braid, and wherein the one or more wires consists of one of: nitinol wire, stainless steel, cobalt chrome, and nylon.

7. An implantable heart valve-adapter delivery system, comprising:

an implantable heart-valve adapter comprising a tubular braided frame, wherein the tubular braided frame comprises an inflow end and an outflow end;

wherein the tubular braided frame extends out from the inflow end to form at least one flange; and wherein the tubular braided frame comprises engagement attachments extending out from and integrally formed with the outflow end, the engagement attachments comprising a leaflet clip and two U-shaped stabilization anchors, wherein the leaflet clip is disposed between the two U-shaped stabilization anchors, wherein when deployed in a native mitral valve comprising a native mitral annulus and one or more native leaflets, the leaflet clip engages behind the one or more native leaflets and the two U-shaped stabilization anchors extend towards the native mitral annulus behind the one or more native leaflets;

a delivery component, comprising one or more suture lines connected on a first end to the engagement attachments;

wherein the one or more suture lines connects on a second end to the delivery component.

8. The system of claim 7, wherein the tubular braided frame is constructed of one or more material that is expandable or compressible or both expandable and compressible.

9. The system of claim 8, wherein the implantable heart-valve adapter comprises a layer of material extending over an outside portion and inside portion of the tubular braided frame, the at least one flange, and the engagement attachments.

10. The system of claim 8, wherein the implantable heart-valve adapter comprises a layer of material extending over an outside and inside portion of the tubular braided frame and the at least one flange.

11. The system of claim 8, wherein the stabilization anchors are between 120 to 180 degrees apart.

12. A method for percutaneous deployment and placement of an implantable heart-valve adapter, comprising:

an implantable heart-valve adapter and a delivery component;

wherein the implantable heart-valve adapter comprises a tubular braided frame, an inflow end and an outflow end;

wherein the tubular braided frame extends out from the inflow end to form at least one flange; and wherein the tubular braided frame extends out from the outflow end to form engagement attachments comprising a leaflet clip and two U-shaped stabilization anchors, wherein the leaflet clip is disposed between the two U-shaped stabilization anchors, wherein the tubular braided frame and at least one of the two-shapted stabilization anchors are integrally formed as a single component;

wherein the delivery component comprises one or more suture lines;

wherein the one or more suture lines goes through the engagement attachments and connects to the delivery component;

percutaneously placing the implantable heart-valve adapter into one of a vein or an artery;

delivering the implantable heart-valve adapter to a native heart valve;

placing the implantable heart-valve adapter in the position of the native heart valve; and expanding the engagement attachments, wherein when deployed in a native mitral valve comprising a native mitral annulus and one or more native leaflets, the leaflet clip engages behind the one or more native leaflets and the two U-shaped stabilization anchors extend towards the native mitral annulus behind the one or more native leaflets.

13. The method of claim 12, wherein the tubular braided frame is constructed of one or more material that is expandable or compressible or both expandable and compressible, and wherein the apparatus comprises a layer of material extending over an outside portion and inside portion of the tubular braided frame, the at least one flange, and the engagement attachments.

13
14

14. The method of claim 13, wherein the vein is a femoral vein and wherein delivering the implantable heart-valve adapter to a native heart valve comprises delivering the implantable heart-valve adapter through the vena cava.

15. The method of claim 13, wherein the vein is a femoral vein and wherein delivering the implantable heart-valve adapter to a native heart valve comprises delivering the implantable heart-valve adapter through the vena cava and through a puncture in the atrial septum.

16. The method of claim 13, wherein percutaneously placing the replacement heart-valve delivery system into one of a vein or an artery consists of inserting the replacement heart-valve delivery system into one of the vein or the artery over a guidewire.

17. The method of claim 13, wherein the stabilization anchors are between 120 to 180 degrees apart.

18. The method of claim 13, wherein the tubular braided frame is a braid of one or more wires, wherein the braid of the one or more wires is either a zig-zag braid or an over-under braid, and wherein the one or more wires consists of one of: nitinol wire, stainless steel, cobalt chrome, and nylon.

* * * * *